United States Patent [19]

Huitema et al.

[11] Patent Number: 5,452,836
[45] Date of Patent: Sep. 26, 1995

[54] SURGICAL STAPLING INSTRUMENT WITH IMPROVED JAW CLOSURE AND STAPLE FIRING ACTUATOR MECHANISM

[75] Inventors: Thomas W. Huitema, Cincinnati; Thomas J. Sierocuk, West Chester, both of Ohio; Eric J. Butterfield, Morrisville, N.C.; Joseph C. Hueil, Loveland, Ohio; Kirk M. Nicola, West Chester, Ohio; Robert L. Koch, Jr., Cincinnati, Ohio

[73] Assignee: Ethicon Endo-Surgery, Inc., Cincinnati, Ohio

[21] Appl. No.: 192,885

[22] Filed: Feb. 7, 1994

[51] Int. Cl.$^6$ ............................................. A61B 17/068
[52] U.S. Cl. ................................ 227/176; 227/8; 227/19
[58] Field of Search ..................................... 227/175, 176, 227/179, 19, 8

[56] References Cited

U.S. PATENT DOCUMENTS

| | | | |
|---|---|---|---|
| 3,080,564 | 3/1963 | Strekopitov et al. | 1/50 |
| 3,275,211 | 9/1966 | Hirsch et al. | 227/124 |
| 3,315,863 | 4/1967 | O'Dea | 227/19 |
| 3,589,589 | 6/1971 | Akopov | 227/153 |
| 4,354,628 | 10/1982 | Green | 227/19 |
| 4,383,634 | 5/1983 | Green | 227/19 |
| 4,402,445 | 9/1983 | Green | 227/19 |
| 4,473,077 | 9/1984 | Noiles et al. | 128/305 |
| 4,508,253 | 4/1985 | Green | 227/19 |
| 4,513,746 | 4/1985 | Aranyi et al. | 227/19 |
| 4,527,724 | 7/1985 | Chow et al. | 227/8 |
| 4,566,620 | 1/1986 | Green et al. | 227/19 |
| 4,591,085 | 5/1986 | Giovanni | 227/8 |
| 4,610,383 | 9/1986 | Rothfuss et al. | 227/19 |
| 4,664,305 | 5/1987 | Blake, III et al. | 227/19 |
| 4,728,020 | 3/1988 | Green et al. | 227/19 |
| 4,869,414 | 9/1989 | Green et al. | 227/19 |
| 4,938,408 | 7/1990 | Bedi et al. | 227/8 |
| 4,941,623 | 7/1990 | Pruitt | 227/19 |
| 5,049,152 | 9/1991 | Simon et al. | 227/19 |
| 5,137,198 | 8/1992 | Nobis et al. | 227/19 |
| 5,318,221 | 6/1994 | Green et al. | 227/19 |
| 5,332,142 | 7/1994 | Robinson et al. | 227/19 |

*Primary Examiner*—Scott A. Smith
*Attorney, Agent, or Firm*—Paul A. Coletti

[57] ABSTRACT

An improved surgical stapling instrument is provided for applying surgical staples to human tissue. The instrument has an articulated stapling head assembly mounted by a rotatable and flexible support shaft on an actuator handle assembly with an improved actuator mechanism for closing and firing the stapling head assembly. The stapling head assembly comprises a fixed jaw with a staple cartridge and a movable jaw with an anvil for clamping the tissue therebetween. The actuator mechanism comprises a jaw closure lever for closing the jaws and a staple firing lever for actuating a staple driver to drive the staples from the staple cartridge into the tissue and against the anvil. The actuator mechanism also includes a cam pulley mounted for rotation by the staple firing lever and secured to a firing cable for actuating the staple driver. A set of drive gears rotatably positioned on opposite sides of the cam pulley mesh with gear sectors on the staple firing lever to rotate the cam pulley and apply tension to the firing cable when the staple firing lever is actuated. The cam pulley has a contoured cam lobe for actuating the firing cable with different mechanical advantages as the pulley is rotated. An anti-backup member engages the cam pulley to prevent the pay-out of the firing cable before and after the staple firing lever is actuated. The length of the support shaft can be adjusted to set the tension in the closure cable so that the jaws are completely closed by the jaw closure lever to produce staples of uniform height when the staple firing lever is actuated.

16 Claims, 19 Drawing Sheets

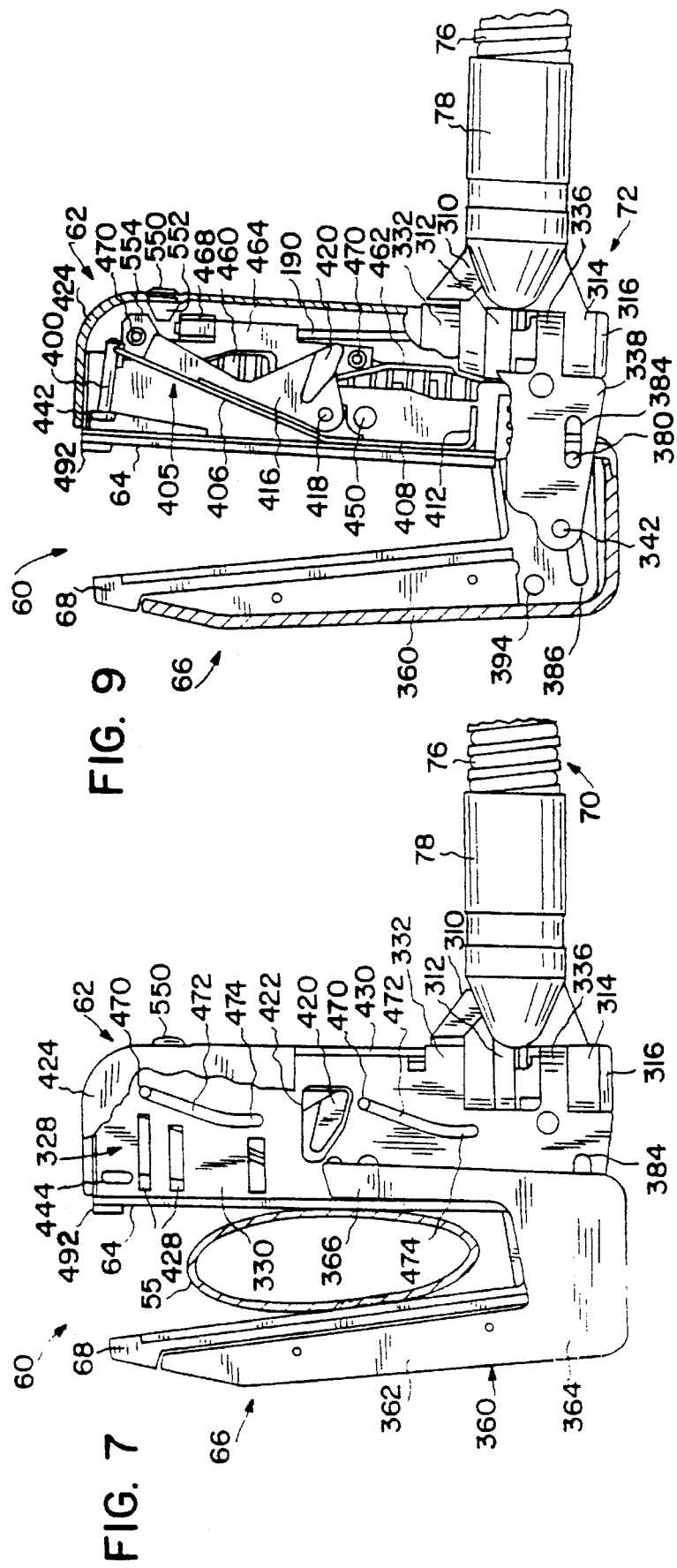

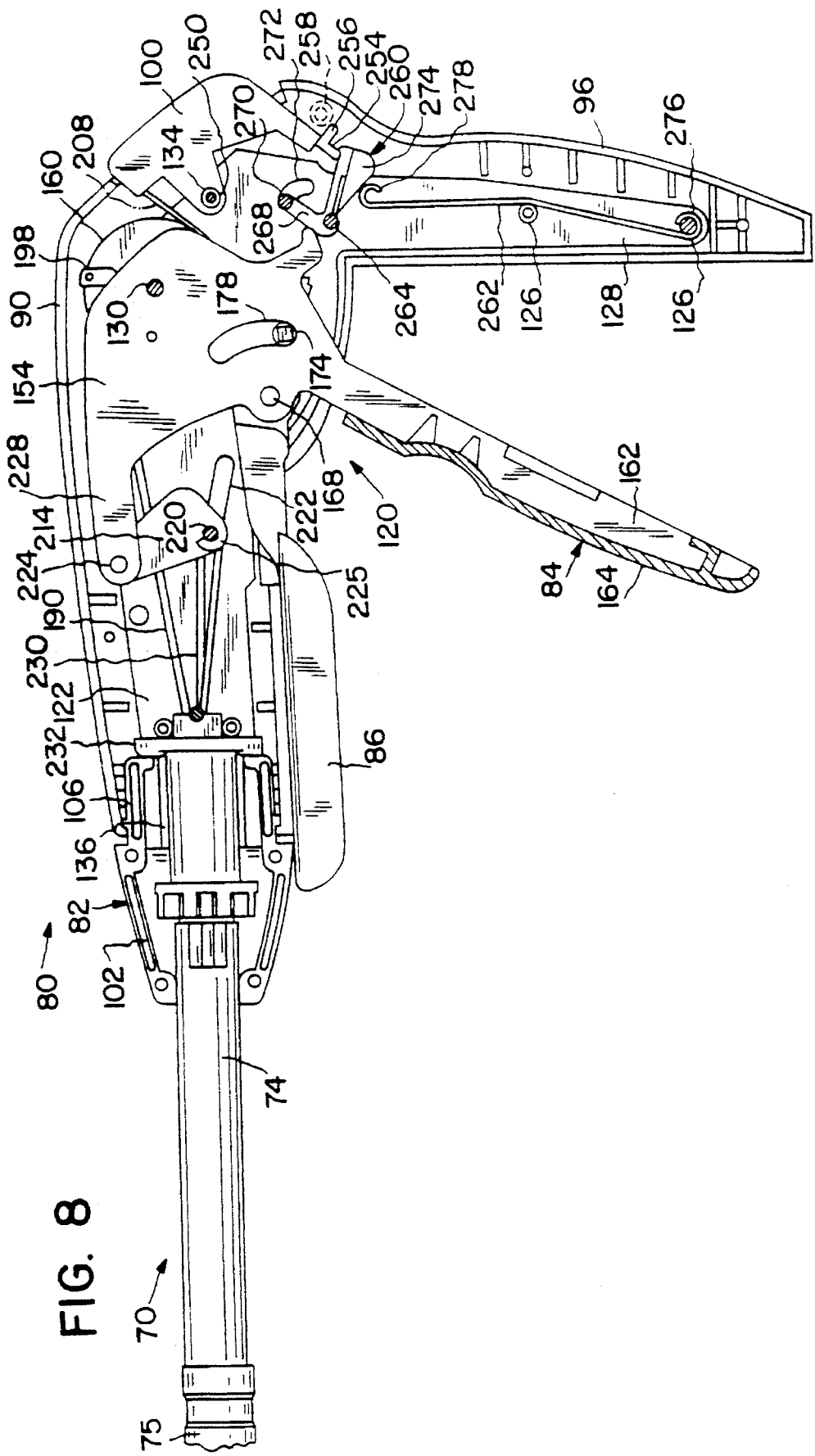

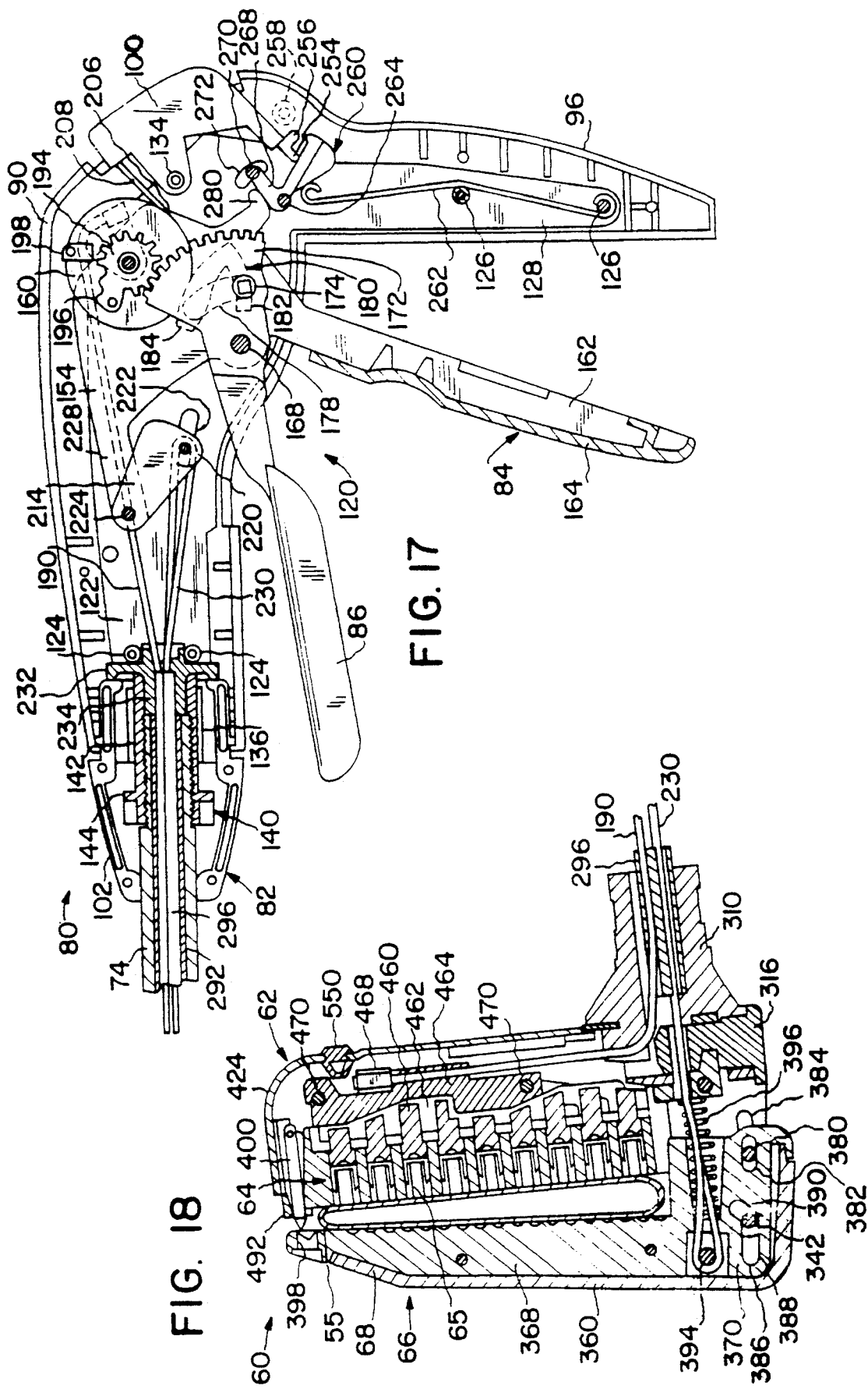

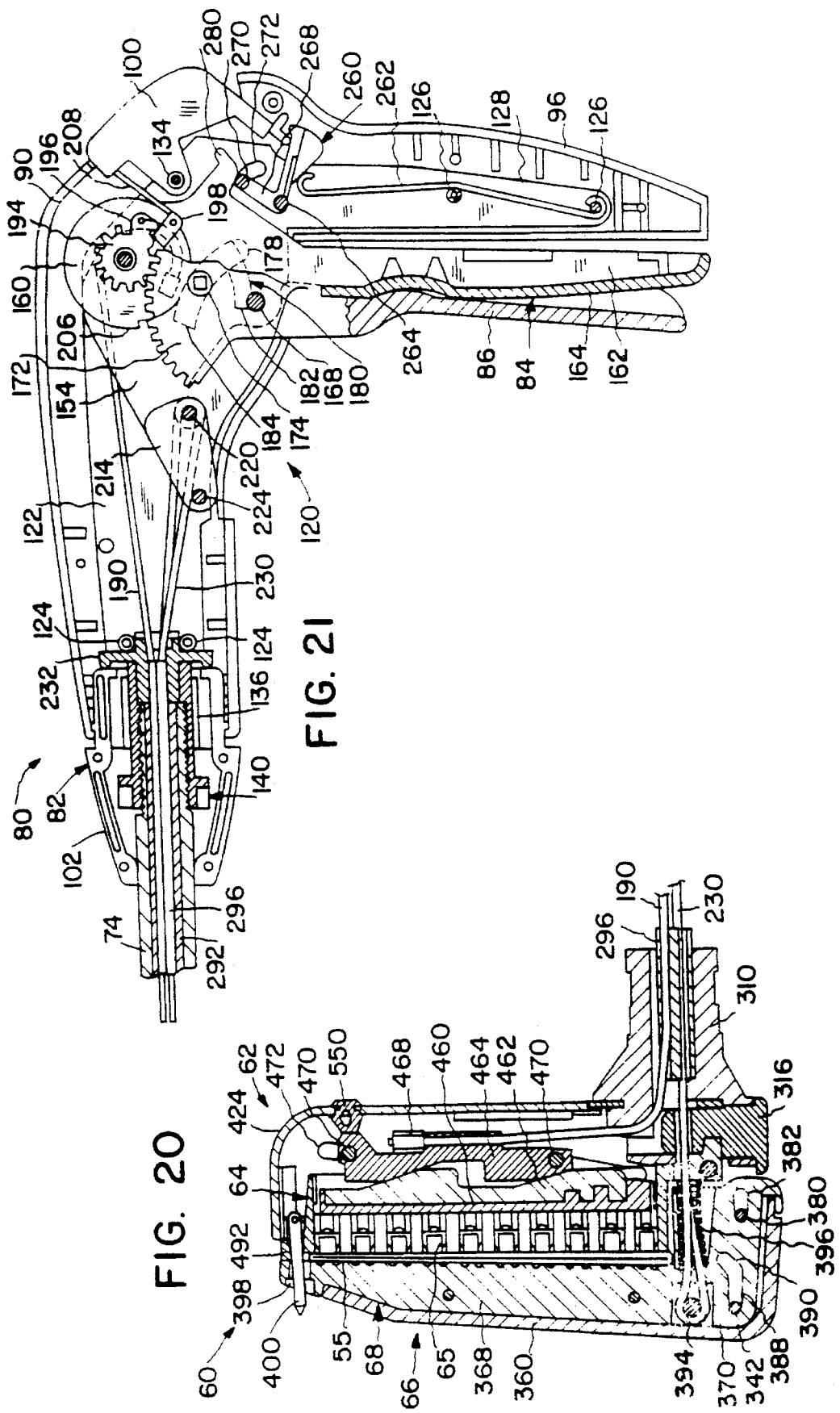

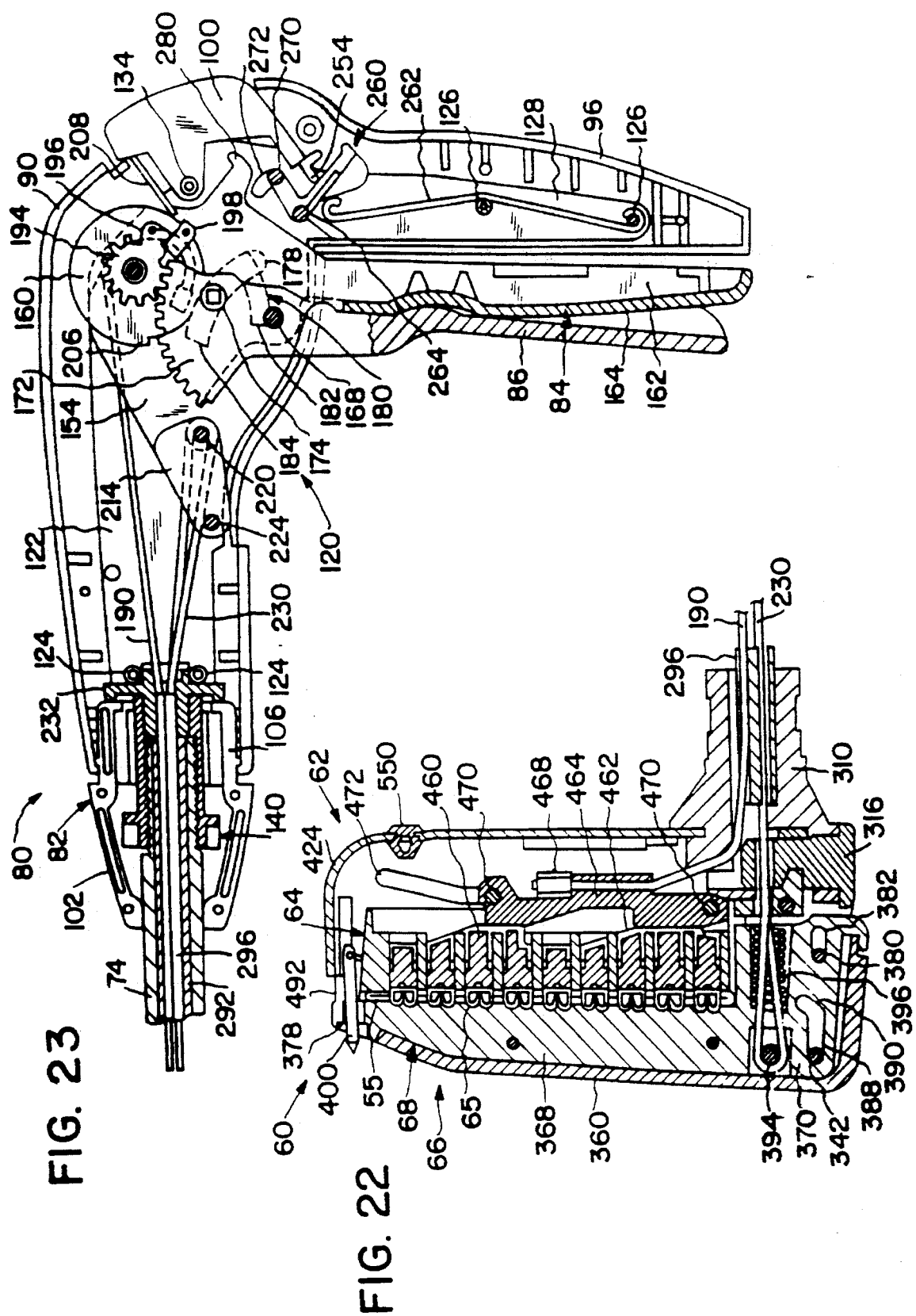

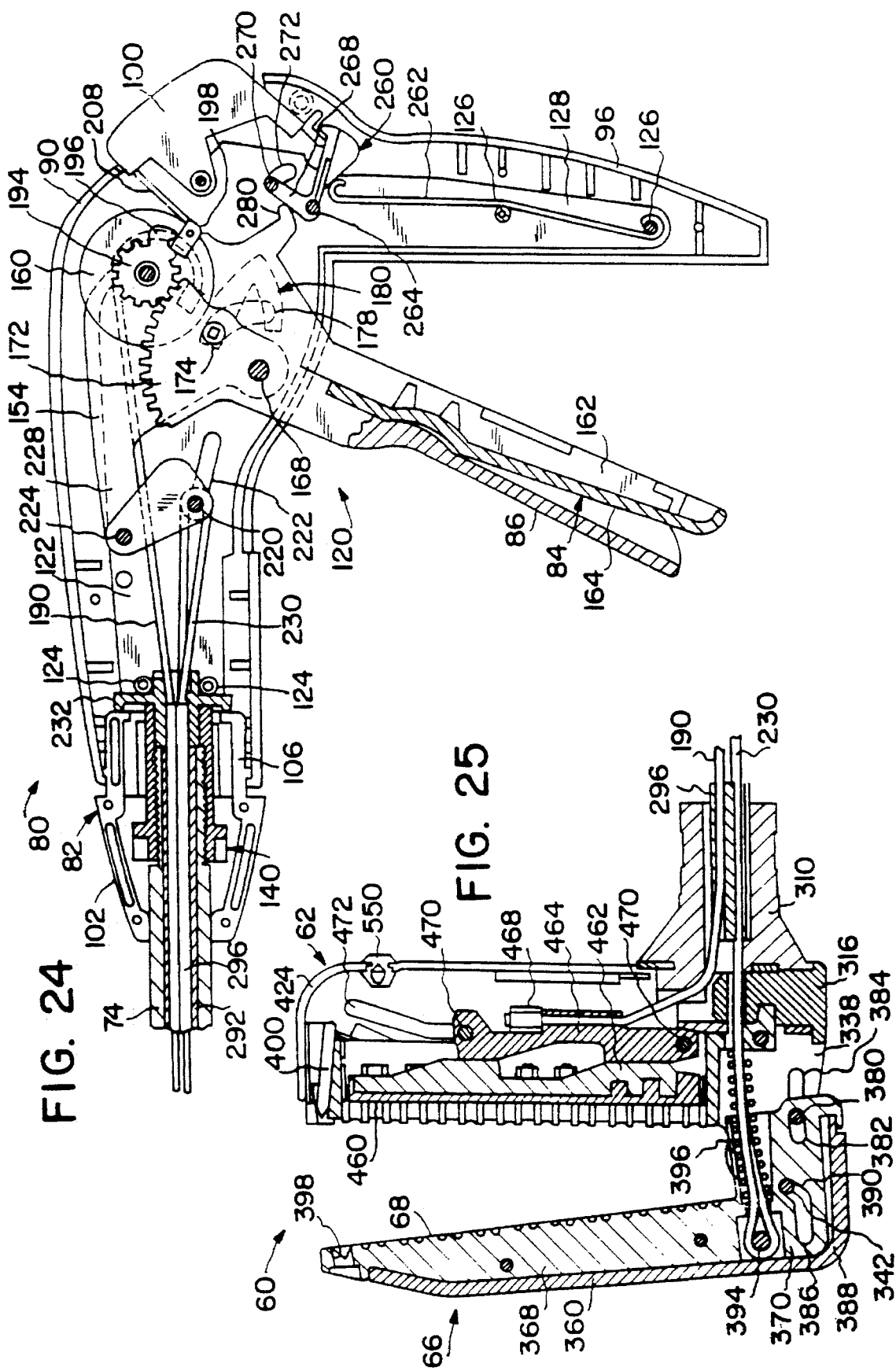

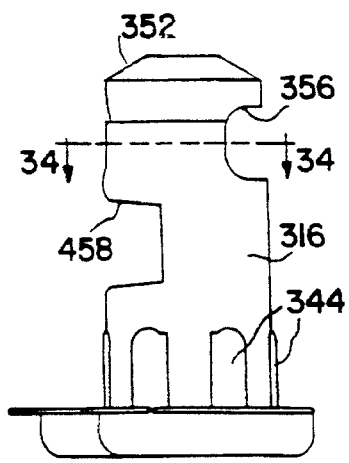
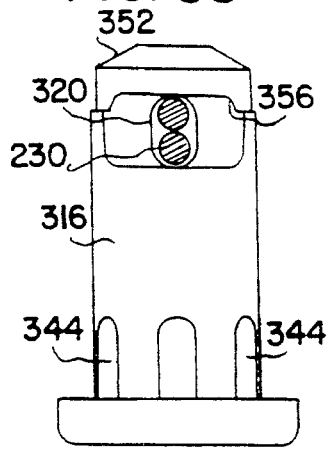
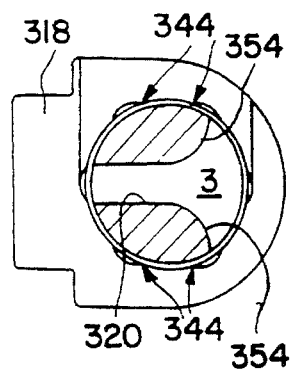
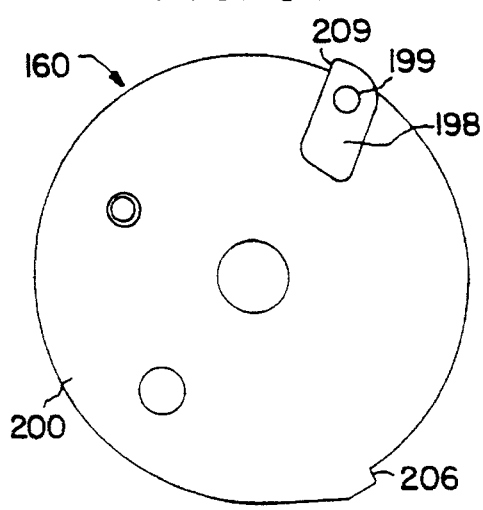
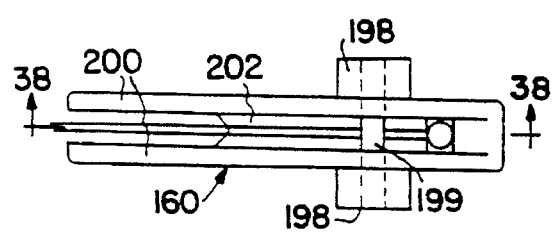
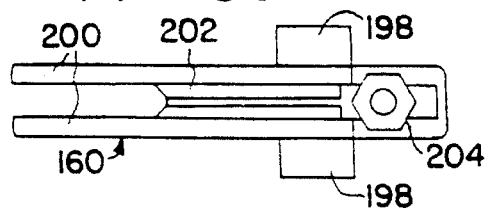
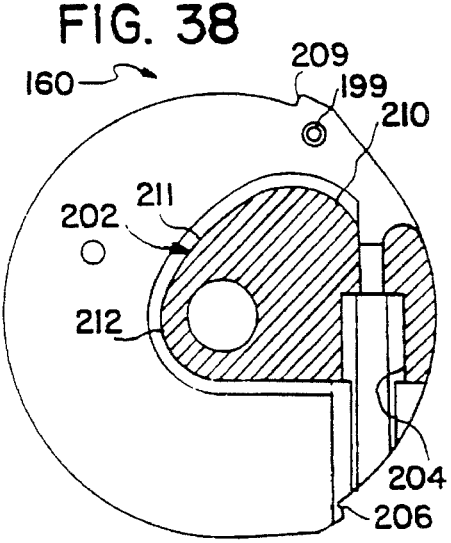

SURGICAL STAPLING INSTRUMENT WITH IMPROVED JAW CLOSURE AND STAPLE FIRING ACTUATOR MECHANISM

FIELD OF THE INVENTION

The present invention generally relates to a surgical instrument for applying surgical fasteners to tissue and, more particularly, to a surgical stapling instrument with an articulated stapling head assembly mounted by a rotatable and flexible support shaft on an actuator handle assembly which includes an improved actuator mechanism for closing and firing the stapling head assembly.

BACKGROUND OF THE INVENTION AND PRIOR ART

In recent years, there has been an increasing number of surgeons using surgical staples, rather than conventional sutures. This is true because the use of surgical staples and surgical stapling instruments has made many difficult procedures much simpler to perform. Of more importance, however, is that the use of surgical staples significantly reduces the time required for most procedures, and therefore reduces the length of time which the patient must be maintained under anesthetic. Many types of surgical stapling instruments have been devised for different surgical procedures.

The present invention is directed to a surgical instrument for applying surgical fasteners to internal organs and tissues such as the lung, esophagus, stomach, duodenum, and intestines. The invention is embodied in a linear surgical stapler which permits access to restricted surgical sites, e.g., the pelvic area of the human body.

In its earliest form, the linear surgical stapling instrument was a permanent, multi-use instrument and the surgical staples were manually loaded into the instrument one at a time. An example of a surgical stapling instrument of this type is disclosed in U.S. Pat. No. 3,080,564. This type of instrument was, in general, complex in construction, expensive to manufacture, heavy, bulky and difficult to both load the surgical staples and to clean and sterilize after each use. A subsequent improvement in linear surgical stapling instruments was the provision of presterilized, disposable loading units or staple cartridges. U.S. Pat. Nos. 3,275,211, 3,315,863 and 3,589,589 disclose examples of permanent, multi-use linear instruments having replaceable staple cartridges.

Several types of surgical fastener applying instruments are known for applying surgical fasteners to body tissue clamped between relatively movable fastener holding and anvil portions of the instrument. The surgical fasteners may be metal staples as shown, for example, in U.S. Pat. No. 3,275,211, or consist of non-metallic resinous materials as shown, for example, in U.S. Pat. No. 4,402,445. In the case of metal staples, the staple legs are typically driven through the tissue and formed by the anvil to secure the staples in the tissue. In the case of non-metallic fasteners, each fastener may initially consist of two separate parts, i.e., a fastener part disposed in the fastener holding part of the apparatus, and a retainer part disposed in the anvil part of the apparatus. The leg or legs of the fastener parts are driven through the tissue and interlock with the retainer parts to secure the fasteners in the tissue. Although most surgical staples are biologically inert and remain permanently in the body, biologically absorbable metal surgical staples are known. Surgical fasteners of nonmetallic resinous materials can also be made either biologically absorbable or non-absorbable.

The surgical instrument of the present invention is not limited to use with any particular type or form of fasteners. The various surgical fasteners mentioned above represent examples of the types of fasteners which can be used with the instrument of the present invention. Thus, as used herein, surgical fastener is meant to be generic to all of the above fasteners, including both staples and two-part devices. Similarly, as used herein, fastener holder and anvil are terms which are generic to surgical instruments for applying the above types of fasteners.

In the prior instruments disclosed in U.S. Pat. Nos. 3,275,211 and 4,402,445 for applying surgical fasteners to tissue clamped between the fastener holding and anvil portions of the instrument, a distal fastener applying assembly is rigidly connected to the proximal actuator portion of the instrument. More recently, however, there has been increasing interest in instruments in which the connection between the fastener applying assembly and the actuator assembly is not completely rigid. U.S. Pat. No. 4,473,077, for example, shows a surgical stapler in which the shaft assembly connected between the fastener applying and actuator assemblies is transversely flexible in a single plane.

Also, in view of rising hospital costs, there has been an ever increasing interest in disposable surgical stapling instruments to eliminate as much work as possible, i.e., disassembly, cleaning, reassembly, sterilization and the like, and to be more efficient, while at the same time, not having to compromise the Surgical procedures. U.S. Pat. Nos. 4,354,628, 4,383,634 and 4,527,724, for example, each disclose disposable linear surgical stapling instruments. A surgical fastener applying apparatus is disclosed in U.S. Pat. No. 4,566,620 including a fastener applying assembly rotatably mounted at the distal end of a longitudinal shaft assembly by a joint for allowing rotation of the fastener applying assembly relative to the actuator assembly about each of three mutually orthogonal axes. U.S. Pat. Nos. 4,728,020 and 4,869,414 also disclose surgical fastener applying instruments.

Additional examples of surgical instruments including a fastener applying assembly provided with relatively movable fastener holding and anvil portions are disclosed in U.S. Pat. Nos. 4,591,085 and 4,941,623. The instrument disclosed in U.S. Pat. No. 4,591,085 includes a trigger interlocking mechanism which precludes the actuation of the trigger until an appropriate gap is set between the jaws of the instrument.

U.S. Pat. No. 4,938,408 discloses a surgical stapling instrument including a rotatable support shaft on which a Stapler head is rotatably mounted for rotation about an axis normal to the axis of the support shaft. U.S. Pat. No. 5,137,198 discloses a linear surgical stapling instrument including a fast jaw closure mechanism and a trigger safety device.

In co-pending U.S. patent application Ser. No. 832,299, filed on Feb. 7, 1992, entitled "Surgical Anastomosis Stapling Instrument With Flexible Support Shaft And Anvil Adjusting Mechanism", assigned to the same assignee as the present invention, a surgical stapling instrument including a flexible shaft assembly is disclosed. The flexible shaft assembly comprises a pair of elongated helical elements which are concentrically wound together with the coils of the first helical element alternately interspersed with the coils of the second helical element. Each coil of the first helical element has a round cross section and each coil of the second helical element has a triangular cross section provided with sloped surfaces which slidably engage the adjacent round coils.

In co-pending U.S. patent application Ser. No. 162,557, filed on Dec. 6, 1993, entitled "Surgical Stapling Instrument With Articulated Stapling Head Assembly On Rotatable And Flexible Support Shaft", assigned to the same assignee as the present invention, a surgical stapling instrument is disclosed which includes an actuator handle assembly with a pivotally mounted jaw closure lever and a staple firing lever pivotally mounted on the jaw closure lever. The jaw closure lever operates a closure cable for closing the jaws of a stapling head assembly to clamp the tissue therein. The staple firing lever operates a firing cable for actuating a staple driver to drive surgical staples from a staple holder into the clamped tissue. A pulley is rotatably mounted on the jaw closure lever. The firing cable travels around the pulley and is secured to the staple firing lever which applies tension to the firing cable when the staple firing lever is actuated. The pulley is not Secured to the firing cable and is not coupled by any drive mechanism for rotation by the staple firing lever.

In manually operated medical instruments, e.g. surgical staplers, it is advantageous to operate within the hand strength and grasp size limitations of the persons who will actually operate the instruments. With many medical instrument functions, such as staple firing, the force or load applied to the actuator cable is nonuniform over the required firing stroke. The load is low during early portions of the stroke when the staples are advancing out of the cartridge and piercing the tissue. Once the staples bottom in the anvil pockets, the resistance and load rise rapidly as the staple legs buckle. Then the resistance and load drop down and rise again as the final forming of the staples into a B-shaped configuration occurs. In contrast, the operator has maximum effective strength at the mid-portion of the stroke of the instrument. At the final portion of the stroke, it is advantageous to require a lower operating force to make it easier to over-travel another lever for reopening of the instrument. In addition, it is easier for the operator to complete the firing stroke if the input load drops off at the end of the stroke.

Accordingly, it is an object of the present invention to provide a surgical instrument for applying surgical fasteners, such as surgical staples, with an improved actuator mechanism which operates within the hand strength and grasp size limitations of the operator.

Another object of the invention is to provide a surgical stapling instrument with an improved actuator mechanism in which a pulley is secured to an actuator cable and rotated by a staple firing lever to fire the staples.

It is also an object of the invention to provide a surgical stapling instrument with an improved actuator mechanism which includes a cam pulley secured to a actuator cable and rotatable by a staple firing lever for operating the actuator cable with different mechanical advantages as the cam pulley is rotated to fire the staples.

A further object of the invention is to provide a surgical stapling instrument with an improved actuator mechanism including a cam pulley secured to an actuator cable and rotatable by a staple firing lever which includes an anti-backup mechanism to prevent the pay-out of the actuator cable before and after the staples are fired.

SUMMARY OF THE INVENTION

The present invention achieves an improved surgical instrument for applying surgical fasteners, such as staples, to human tissue which is particularly suited for applying one or more rows of fasteners across a tissue lumen to produce a fluid tight closure of the lumen. The surgical instrument of this invention is intended for use in thoracic and abdominal surgical procedures in which single fire surgical staplers are currently used and where access to the surgical site is restricted. For example, the surgical instrument can be used in the following types of procedures: (1) a double stapling technique, especially for a low anterior re-section, (2) closure of the bronchus during a lobectomy or pneumonectomy, (3) closure of the esophagus in esophageal procedures, and (4) closure of the pulmonary blood vessels during a lobectomy or pneumonectomy.

The present invention is embodied in a surgical stapling instrument for applying one or more surgical staples to tissue which comprises a stapling head assembly including a first jaw with a staple holder for receiving one or more surgical staples, a second jaw with an anvil for clamping the tissue against the staple holder when the jaws are closed, and a staple driver for driving the staples from the staple holder into the tissue and against the anvil, and an actuator handle assembly including a jaw closure lever for closing the jaws and a staple firing lever for actuating the staple driver. The stapling instrument includes a closure cable operable by the jaw closure lever for closing the jaws to clamp the tissue between the anvil and the staple holder and a firing cable operable by the staple firing lever for actuating the staple driver to drive the staples into the tissue and against the anvil. A pulley is rotatably mounted on the actuator handle assembly and secured to the firing cable for applying tension to the firing cable when the pulley is rotated by the staple firing lever to actuate the staple driver.

In a preferred embodiment, the stapling instrument includes drive means coupling the staple firing lever to the pulley and rotating the pulley when the staple firing lever is actuated to apply tension to the firing cable to actuate the staple driver. The drive means comprises a pair of drive gears rotatably positioned on opposite sides of the pulley and provided with a set of drive lugs positioned for movement into engagement with a set of side lugs on the pulley when the drive gears are rotated. A pair of gear sectors on the staple firing lever is engaged with the drive gears for rotating the drive gears when the staple firing lever is actuated to move the drive lugs into engagement with the side lugs to rotate the pulley and to apply tension to the firing cable.

In the preferred embodiment of the stapling instrument, the pulley includes a contoured cam lobe for actuating the firing cable with different mechanical advantages as the pulley is rotated. Preferably, the cam lobe includes a first cam region with a large lobe height to provide a small mechanical advantage for actuating the firing cable, a second cam region with an intermediate lobe height which provides an increasing mechanical advantage, and a third cam region with a small lobe height which provides a large mechanical advantage.

In accordance with another aspect of the invention, the stapling instrument includes anti-backup means for engaging the pulley to prevent the pay-out of the firing cable before and after the staple firing lever is actuated. Preferably, an anti-backup member is located on the actuator handle assembly adjacent to the periphery of the pulley. A first detent on the pulley engages the anti-backup member to stop the rotation of the pulley in a first position and prevent the pay-out of the firing cable before the firing lever is actuated. A second detent on the pulley engages the anti-backup member to stop the rotation of the pulley in a second position and prevent the pay-out of the firing cable after the firing lever is actuated.

In accordance with another feature of the invention, the surgical instrument includes latch means mounted on the actuator handle assembly for latching the jaw closure lever in a closed position when the jaws are closed, and a manually operable release button mounted on the actuator handle assembly for actuating the latch means to unlatch the jaw closure lever and allow the jaw closure lever to return to an open position to open the jaws. Preferably, the release button includes an anti-backup member which extends adjacent to the periphery of the pulley for engaging the first and second detents before and after the staple firing lever is actuated to prevent the pay-out of the firing cable.

In a preferred embodiment of the surgical stapling instrument, a support shaft assembly is provided for mounting the stapling head assembly on the actuator handle assembly. The stapling head assembly includes a proximal jaw which supports a staple holder for receiving one or more surgical staples, a distal jaw which supports an anvil for clamping the tissue against the staple holder when the jaws are closed, a staple driver for driving the staples into the tissue and against the anvil, and a firing cam for actuating the staple driver. The actuator handle assembly includes a jaw closure lever pivotally mounted thereon for closing the jaws and a staple firing lever pivotally mounted on the jaw closure lever for actuating the staple driver. The stapling instrument includes a closure cable connected to the distal jaw and operable by the jaw closure lever for moving the distal jaw relative to the proximal jaw to clamp the tissue between the anvil and the staple holder. The stapling instrument also includes a firing cable connected to the firing cam and operable by the staple firing lever for actuating the staple driver to drive the staples into the tissue and against the anvil. A pulley is rotatably mounted on the actuator handle assembly and secured to the firing cable for applying tension to the firing cable when the pulley is rotated by the staple firing lever to actuate the firing cam and the staple driver.

In accordance with another feature of the actuator handle assembly, the surgical instrument includes a control link slidably and pivotally mounted on the actuator handle assembly and operable by the jaw closure lever for applying tension to the closure cable to pull the distal jaw toward the proximal jaw. Preferably, the closure cable comprises a continuous belt with loops at its opposite ends connected to the distal jaw and to the control link.

In a preferred embodiment of the stapling head assembly, the distal jaw includes an anvil member having an upstanding anvil arm and a base portion provided with one or more elongated slots for receiving one or more slide pins to connect the anvil member to the proximal jaw. The distal jaw also includes a shroud member including a pair of side plates which span the opposite sides of the base member and retain the slide pins in the guide slots. Also, in the stapling head assembly, detent means is provided for retaining the firing cam in an unfired position before the staple firing lever is actuated.

Preferably, the shaft assembly is rotatable about its longitudinal axis to orient the stapling head assembly in different angular orientations relative to the actuator handle assembly. A cable support member mounted inside the shaft assembly includes a pair of longitudinal passageways for receiving the firing cable and the closure cable. The cable support member is capable of twisting when the shaft assembly is rotated about its longitudinal axis to prevent the firing cable and the closure cable from twisting together.

In accordance with another aspect of the invention, the stapling instrument includes means for adjusting the length of the shaft assembly to set the tension in the closure cable to close the jaws when the jaw closure lever is actuated. The shaft assembly is adjusted in length during the assembly of the instrument to provide sufficient tension in the closure cable so that the jaws are completely closed by the jaw closure lever to produce a uniform staple height when the staple firing lever is actuated.

BRIEF DESCRIPTION OF THE DRAWINGS

The foregoing and other objects, aspects and advantages will be better understood from the following detailed description of the preferred embodiments of the invention with reference to the drawings, in which:

FIG. 3 is a side view of the flexible section of the support shaft assembly of FIG. 2 in a bent configuration to adjust the orientation of the stapling head assembly;

FIG. 7 is an enlarged, partially cutaway side elevation of the stapling head assembly of FIG. 2;

FIG. 8 is a partially cutaway side view of a jaw closure lever within the actuator mechanism of FIG. 6;

FIG. 9 is an enlarged, partially cutaway side view of a tissue retaining pin mechanism within the stapling head assembly of FIG. 2;

FIG. 17 is a partially cutaway side view showing the actuator mechanism in a partially closed position;

FIG. 18 is an enlarged, partially cutaway side view showing the stapling head assembly in a partially closed position;

FIG. 20 is an enlarged, partially cutaway side view showing the stapling head assembly in a closed and ready to fire position;

FIG. 21 is a partially cutaway side view showing the actuator mechanism in a closed and fired position;

FIG. 22 is an enlarged, partially cutaway side view showing the stapling head assembly in a closed and fired position;

FIG. 23 is a partially cutaway side view showing the actuator mechanism in an over-travel position;

FIG. 24 is a partially cutaway side view showing the actuator mechanism in a fired and re-opened position;

FIG. 25 is an enlarged, partially cutaway side view showing the stapling head assembly in a re-opened position;

FIG. 32 is an enlarged side view of a pin in the pivot connection of the stapling head assembly;

FIG. 33 is a rear view of the pivot pin of FIG. 32; FIG. 34 is a horizontal section of the pivot pin along line 34—34 of FIG. 32; FIG. 35 is an enlarged side view of a cam pulley of the actuator mechanism; FIG. 36 is a bottom view of the cam pulley of FIG. 35; FIG. 37 is a top view of the cam pulley of FIG. 35; FIG. 38 is a vertical section of the cam pulley along line 38—38 of FIG. 37.

DETAILED DESCRIPTION OF PREFERRED EMBODIMENTS

Figure 1:
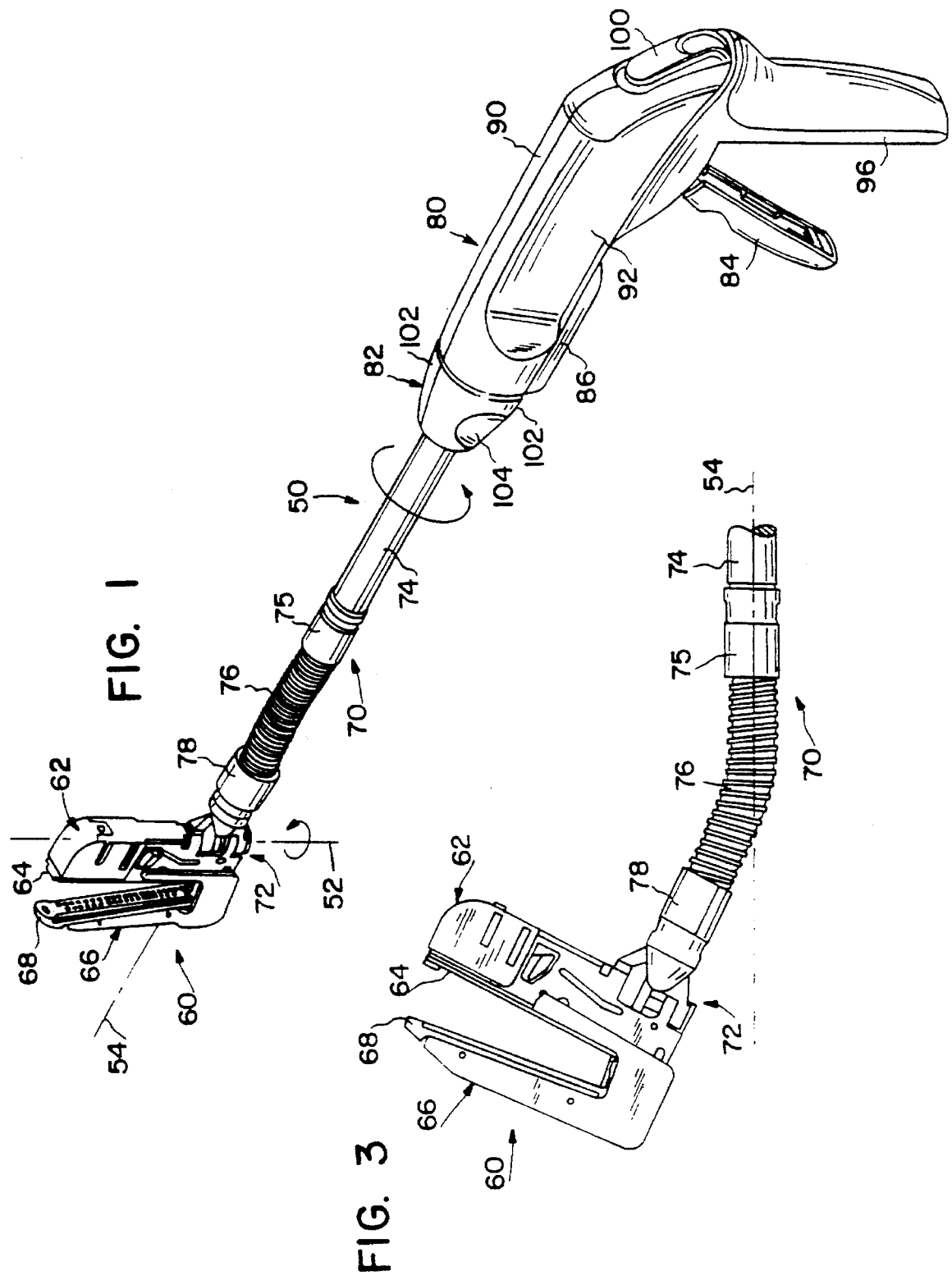
FIG. 1 is a perspective view of a surgical stapling instrument constructed in accordance with this invention including a support shaft assembly with a flexible section for mounting a stapling head assembly on an actuator handle assembly.
Figure 2:
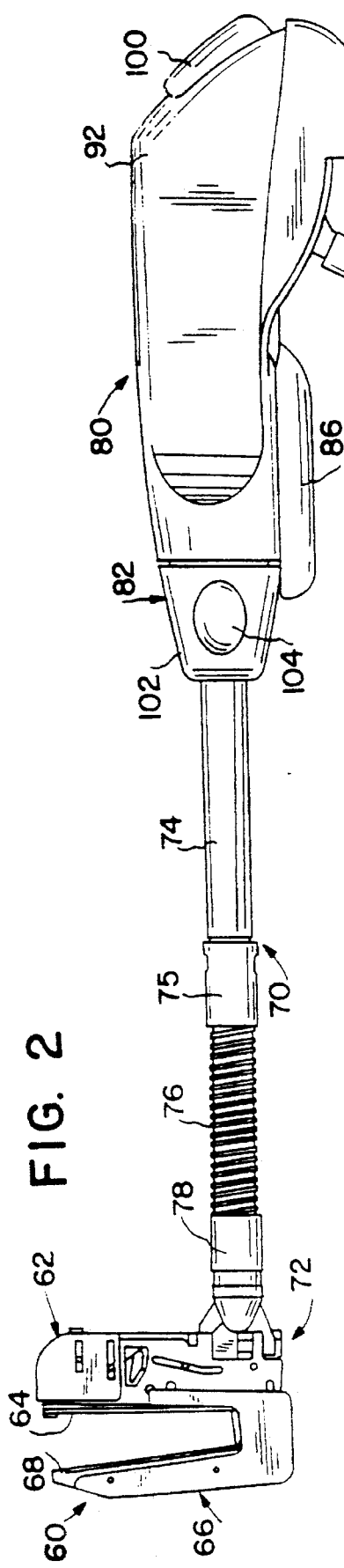
FIG. 2 is a side elevation of the surgical stapling instrument of FIG. 1.

Referring to FIG. 1, the present invention is embodied in a surgical stapling instrument, generally 50, which includes a distal stapling head assembly 60 connected by a support shaft assembly 70 to a proximal actuator handle assembly 80. The stapling head assembly 60 includes a proximal or fixed jaw 62 which supports a staple cartridge 64 and a distal or movable jaw 66 which supports a staple forming anvil 68 (FIG. 2). The staple cartridge 64 receives one or more rows of staples 65 (FIG. 17) which are driven against the anvil 68 and formed into a B-shaped configuration to fasten tissue together. For example, nineteen staples are held in the staple cartridge 64 and arranged in two staggered rows. It will be understood by persons skilled in the art that the surgical stapling instrument 50 can be adapted to operate with two-part surgical fasteners instead of the staples 65.

As shown in FIG. 1, the proximal or fixed jaw 62 is mounted in a hinge-like fashion on a pivot connection 72 which permits the stapling head assembly 60 to pivot about a vertical axis 52 into different angular orientations relative to a centerline or longitudinal axis 54 of the support shaft assembly 70. For example, the pivot connection 72 is arranged to allow the stapling head assembly 60 to pivot about the vertical axis 52 in approximately 20° increments. The articulated stapling head assembly 60 is pivotable either clockwise or counterclockwise about the vertical axis 52 to positions oriented at about ±20°, ±40°, ±60° and ±80° relative to the longitudinal axis or centerline 54. The support shaft assembly 70 is rotatably mounted on the actuator handle assembly 80 for rotation about the longitudinal axis or centerline 54. Preferably, the support shaft assembly 70 is rotatable over an angular range of approximately 180° or more about the centerline 54. A control knob 82 is coupled to the support shaft assembly 70 and rotatably mounted at the distal end of the actuator handle assembly 80 to allow the support shaft assembly 70 to be rotated about its axis 54 to adjust the rotational orientation of the stapling head assembly 60.

The shaft assembly 70 includes a tubular support shaft 74 rotatably mounted on the actuator handle assembly 80 and secured by a coupling sleeve 75 to a flexible tubular shaft 76. The flexible tubular shaft 76 is capable of bending in any radial direction relative to the centerline 54 of the shaft assembly 70 into a bent or curved shape (FIG. 3). The hinge-like pivot connection 72 is mounted on a coupling sleeve 78 at the distal end of the flexible shaft 76. The tubular support shaft 74 can be made of plastic material. The central coupling sleeve 75 and the distal coupling sleeve 78 can be made of metal, e.g., aluminum.

The actuator handle assembly 80 includes a pivotally mounted closure lever 84 for closing the movable jaw 66 toward the fixed jaw 62 to clamp a tubular section of tissue between the jaws 62 and 66. The actuator handle assembly 80 also includes a pivotally mounted firing lever 86 for actuating the stapling head assembly 60 to drive the staples from the staple cartridge 64 through the tissue and to form the staples against the anvil 68.

As shown in FIG. 1, the actuator handle assembly 80 includes a pair of hollow handle sections 90 and 92 made of plastic material which can be welded or snap fit together. Each of the handle sections 90 and 92 includes a proximal depending handle grip 96. A manually operable release button 100 protrudes upwardly at the proximal end of the actuator handle assembly 80.

Figure 15:
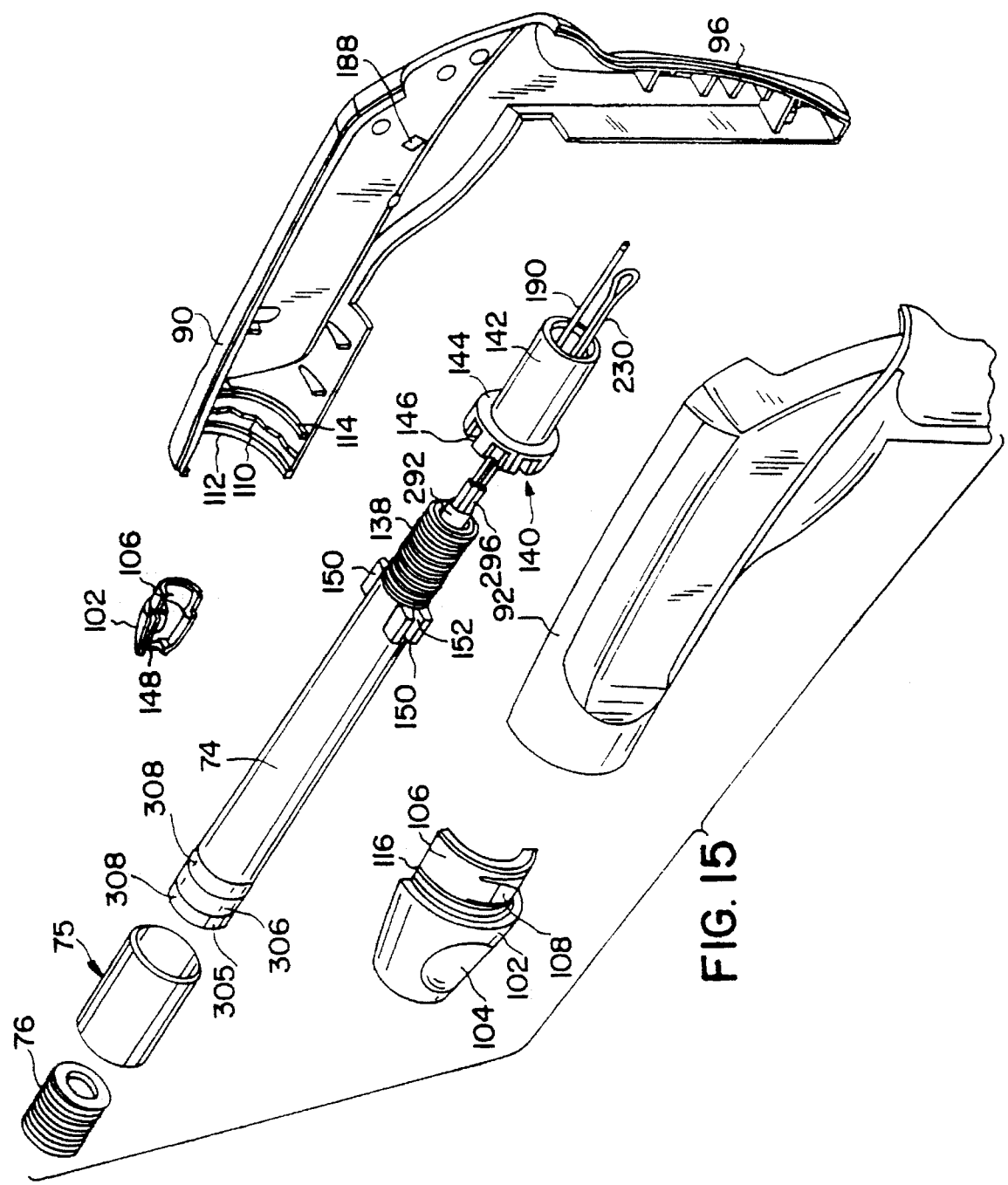
FIG. 15 is an exploded perspective view of a shaft adjusting mechanism in the actuator handle assembly of FIG. 6.

Referring to FIGS. 1 and 15, the control knob 82 comprises a pair of hollow tapered cylindrical half-Sections 102 made of plastic material which can be welded or snap fit together. Each of the knob half-sections 102 has a recessed finger grip area 104 which facilitates the manual engagement and operation of the control knob 82. Also, each knob half-section 102 has a semi-circular proximal flange 106 provided with a resilient finger which projects radially outward from the semi-circular flange 106. Each radially projecting finger 108 engages a series of serrations or teeth 110 which are arranged along a semi-circular path adjacent to the distal end of each of the handle sections 90 and 92. The resilient fingers 108 and the serrations 110 provide a detent mechanism which defines fourteen angular positions uniformly spaced apart for rotation of the shaft assembly 70.

When the knob half-sections 102 are assembled together and inserted into the distal end of the actuator handle assembly 80, the semi-circular flanges 106 form a hub which is rotatably supported by an inwardly projecting semi-circular flange 112 formed at the distal end of each of the handle sections 90 and 92. Also, the semi-circular flanges 106 are rotatably supported by a semi-circular rib 114 formed on the interior of each of the handle sections 90 and 92. The semi-circular flanges 112 and the semi-circular ribs 114 provide bearing surfaces to facilitate the rotation of the control knob 82. In addition, a semi-circular ridge 116 formed on the outside of each semi-circular flange 106 is located inside the semi-circular flange 112 at the proximal end of each of the handle sections 90 and 92 to limit the axial displacement of the control knob 82 relative to the handle assembly 80.

Figure 14:
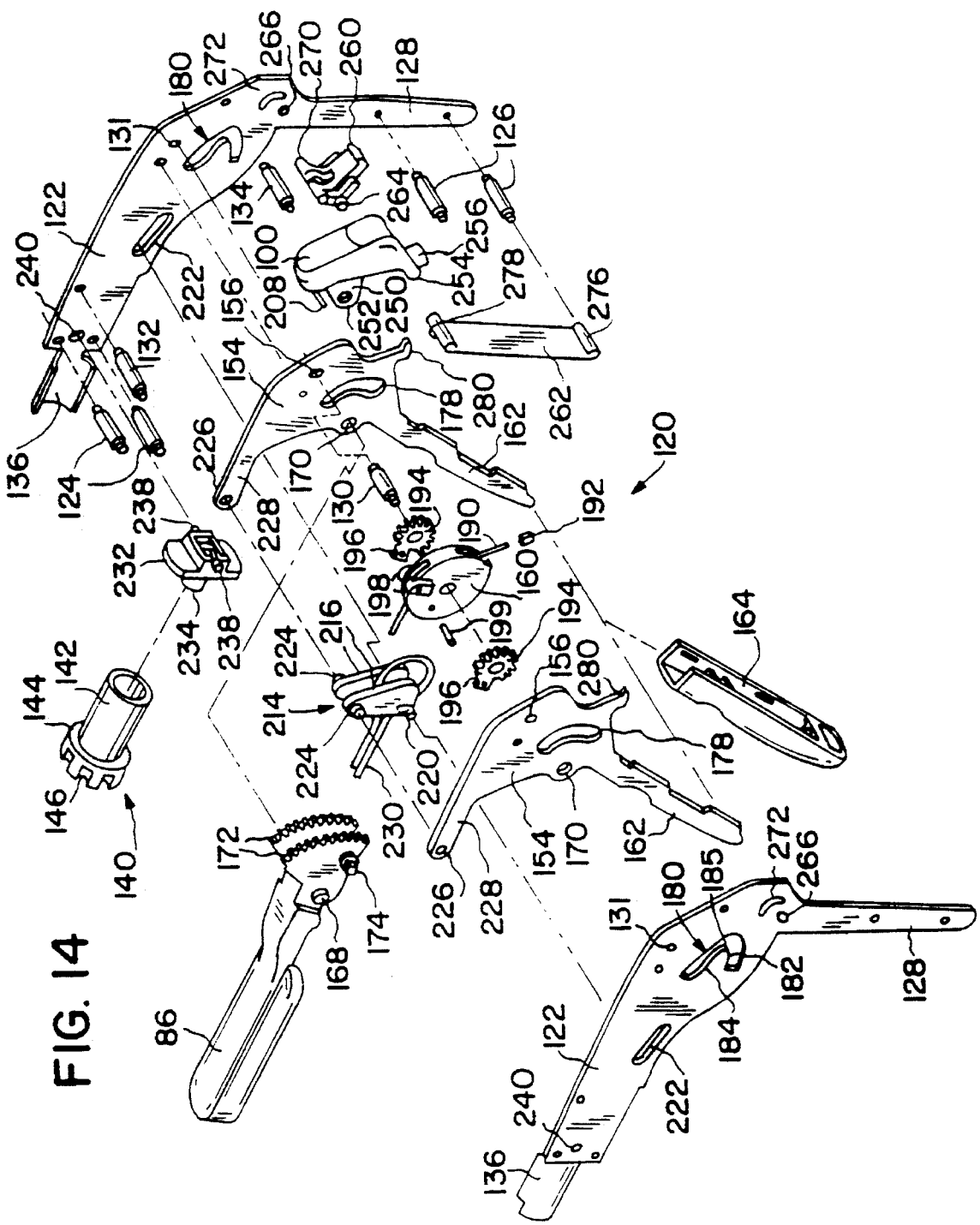
FIG. 14 is an exploded perspective view showing the components of the actuator mechanism in the actuator handle assembly of FIG. 6.

Referring to FIGS. 1 and 14, the actuator handle assembly 80 includes an actuator mechanism, generally 120, contained within the hollow plastic handle sections 90 and 92. The actuator mechanism 120 includes a pair of outer support plates 122 which are similar in shape to the handle sections 90 and 92. Each of the handle sections 90 and 92 is provided with a set of internal flanges and ribs which support the support plates 122 in a fixed position within the actuator handle assembly 80 when the handle sections 90 and 92 are assembled together. Alternatively, the features of the support plates 122 can be integrally formed on the interior of the handle sections 90 and 92. The support plates 122 are fastened together in a spaced parallel relationship by a pair of transverse connecting pins 124 located adjacent to the distal ends of the support plates 122 and by a pair of connecting pins 126 extending transversely between a pair of depending grip portions 128 of the support plates 122. A double step pivot pin 130 is mounted in a pair of holes 131 formed in the top proximal portions of the support plates 122 and pivotally supports the other components of the actuator mechanism 120. The support plates 122 are also joined together by a front connecting pin 132 and a rear connecting pin 134 which pivotally supports the release button 100. A pair of opposed semi-circular flanges 136 which extend axially from the distal ends of the support plates 122 are received between the semi-circular flanges 106 of the knob half-sections 102 (FIG. 8).

Figure 10:
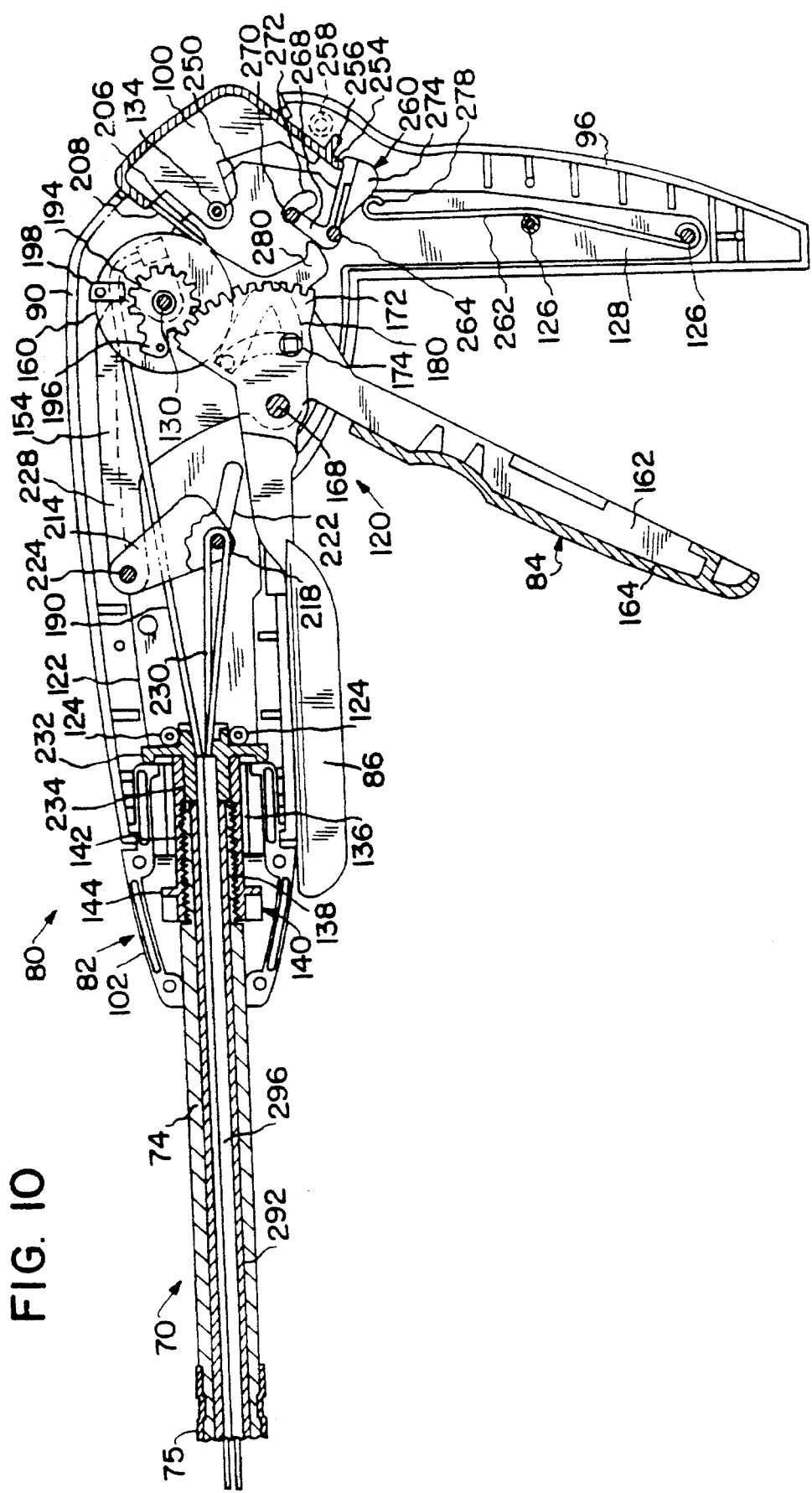
FIG. 10 is a partially cutaway side view of a stapling firing lever in the actuator mechanism of FIG. 6.

As shown in FIGS. 10 and 15, the tubular support shaft 74 has a threaded proximal end 138 which is threadably received in an adjusting nut 140 having an elongated tubular body 142 located between the semi-cylindrical flanges 136 of the support plates 122. The adjusting nut 140 has an enlarged distal end 144 provided with a series of circumferentially spaced longitudinal grooves 146 which are adapted to receive a pair of opposed longitudinal ribs 148 (one shown) formed on the inside of the knob half-sections 102. Similarly, the tubular support shaft 74 has a pair of diametrically opposed flanges 150 adjacent to its threaded proximal end 138 which are provided with longitudinal grooves 152 for receiving the longitudinal ribs 148 on the inside of the knob half-sections 102. The adjusting nut 140 allows the effective length of the support shaft assembly 70 to be adjusted by rotation of the adjusting nut 140 on the threaded proximal end 138 of the tubular support shaft 74 during the assembly of the stapling instrument 50. After the adjusting nut 140 is rotated to set the desired shaft length, the knob half-sections 102 are assembled together at the proximal end of the tubular support shaft 74. The longitudinal ribs 148 which are received in the longitudinal grooves 146 and 152 prevent any relative rotation between the tubular support shaft 74 and the adjusting nut 140 after the assembly of the stapling instrument 50 to maintain the desired shaft length.

Referring to FIG. 14, the actuator mechanism 120 includes a pair of closure lever plates 154 each including a pivot hole 156 for receiving the double step pivot pin 130 to pivotally support the closure lever plates 154 for pivotal movement relative to the support plates 122. The closure lever plates 154 are maintained in a spaced parallel relationship by the double step pivot pin 130 which rotatably supports a cam pulley 160. The closure lever places 154 include elongated depending lever portions 162 which are contained inside a hollow plastic closure lever shroud 164 (FIG. 6) to provide the jaw closure lever 84 of the actuator handle assembly 80.

As shown in FIG. 14, the staple firing lever 86 is pivotally mounted between the closure lever plates 154 by a pair of transverse pivot pins 168 (one shown) extending from its opposite sides and rotatably received in a pair of pivot holes 170 (one shown) formed in the closure lever plates 154. The staple firing lever 86, preferably made of molded plastic material, includes a pair of gear sectors 172 which are spaced apart to receive the cam pulley 160 therebetween. A pair of firing lever deployment pins 174 extend transversely from the opposite sides of the gear sector 172. The firing lever deployment pins 174 are slidably received in a pair of arc-shaped slots 178 formed in the closure lever plates 154. The outer ends of the firing lever deployment pins 174 extend through the arc-shaped slots 178 into a pair of firing lever deployment cam slots 180 formed in the support plates 122. Each cam slot 180 includes a lower cam track section 182 and an upper cam track section 184 which intersect at a rear corner 185.

Figure 40:
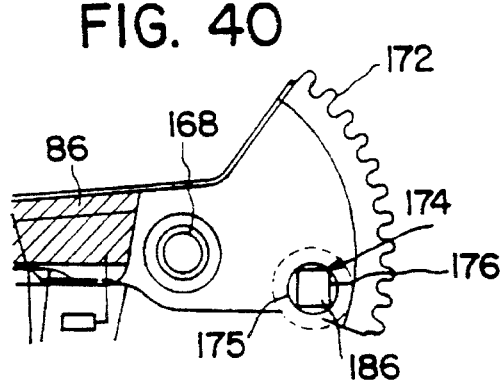
FIG. 40 is an enlarged fragmentary view of the staple firing lever of FIG. 10.

As shown in FIG. 40, each firing lever deployment pin 174 has a cylindrical base 175 which is slidably received in the corresponding arc-shaped slot 178 of the closure lever plate 154. The outer end of each deployment pin 174 comprises a rectangular block 176 which is slidably received in the corresponding cam slot 180 of the support plate 122. On the outer edge of the rectangular block 176 is a diagonal cam 186 which cooperates with a rectangular ledge 188 (FIG. 15) formed on each of the handle sections 90 and 92 to provide a detent mechanism to control the action of the staple firing lever 86.

Referring to FIG. 14, a staple firing cable 190 is anchored to the cam pulley 160 by a cable crimp member 192 at the proximal end of the firing cable 190. Preferably, the firing cable 190 is made of stainless steel and the cable crimp member 192 is made of stainless steel which is crimped onto the staple firing cable 190. Before crimping, the cable crimp member 192 is cylindrical in shape with an axial bore for receiving the staple firing cable 190. After the staple firing cable 190 is inserted, the cable crimp member 192 is crimped, for example, into a hexagonal cross section. The hexagonal cable crimp member 192 is anchored to the cam pulley 160 to apply tension to the firing cable 190 when the cam pulley 160 is rotated.

As shown in FIG. 14, the actuator mechanism 120 includes a pair of drive gears 194 which mesh with the gear sectors 172 of the staple firing lever 86. The drive gears 194 are positioned on opposite sides of the cam pulley 160 and are rotatable about the pivot pin 130. Each of the drive gears 194 has a drive lug 196 for movement into engagement with a pair of side lugs 198 at the top of the cam pulley 160 when the drive gears 194 are rotated. Initially, the drive gears 194 are free to rotate relative to the cam pulley 160 until the drive lugs 196 on the drive gears 194 engage the side lugs 198 on the cam pulley 160. When the drive lugs 196 and the side lugs 198 are engaged, the drive gears 194 and the cam pulley 160 rotate together in a clockwise direction to apply tension to the staple firing cable 190.

Referring to FIGS. 35–38, the cam pulley 160 comprises a pair of disc-shaped side members 200 which are integrally formed with and separated by an interior cam member 202. The cam member 202 has a hexagonally shaped passage 204 in which the hexagonal cable crimp member 192 is anchored to secure the firing cable 190 to the cam pulley 160. The cam pulley 160 has a first set of teeth 206 formed at the periphery of the disc-shaped side members 200 which engage an anti-backup tang 208 on the release button 100 to hold the cam pulley 160 in position during storage and prior to the firing of the stapling instrument 50. The cam pulley 160 has a second set of teeth 209 formed at the periphery of the disc-shaped side members 200 which engage the anti-backup tang 208 after the stapling instrument 50 is fired to control the pay-out of the staple firing cable 190. The side lugs 198 extend radially at the periphery of the disc-shaped side members 200 and are aligned with the second set of teeth 209. A tubular spring pin 199 is inserted in a pair of holes in the side lugs 198.

In another embodiment of the actuator mechanism 120, the anti-backup tang 208 can be eliminated from the release button 100 (FIG. 14) and the cam pulley 160 can be formed without the first and second teeth 206 and 209 (FIG. 38) to eliminate the anti-backup feature. Also, the drive gears 194 can be formed on the cam pulley 160 to reduce the number of components in the actuator mechanism 120.

As shown in FIG. 38, the interior cam member 202 of the cam pulley 160 comprises a contoured cam lobe of varying height for actuating the firing cable 190 with different mechanical advantages as the pulley 160 is rotated. The cam lobe 202 includes a first cam region 210 with a large lobe height to provide a small mechanical advantage for actuating the firing cable 190, a second cam region 211 with an intermediate lobe height which provides an increasing mechanical advantage, and a third cam region 212 with a small lobe height which provides a large mechanical advantage. The cam region 210 engages the staple firing cable during the initial portion of the stroke of the staple firing lever 86 and the cam region 212 engages the staple firing cable 190 during the final portion of the stroke of the staple firing lever 86.

Figure 41:
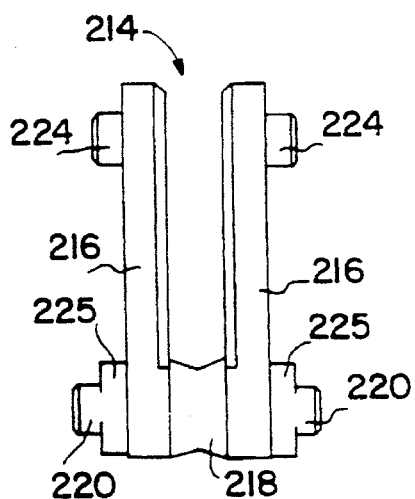
FIG. 41 is an enlarged front view of a control link of the actuator mechanism.

Referring to FIGS. 14 and 41, the actuator mechanism 120 includes a closure control link 214 comprising a pair of triangularly shaped side members 216 which are joined together in a spaced parallel relationship by an integrally formed bridge pin 218. A first pair of pivot pins 220 extend transversely in opposite directions from the lower end of the link 214. The outer ends of the pivot pins 220 are slidably received in a pair of inclined guide slots 222 formed in the support plates 122. A second pair of pivot pins 224 at the upper end of the link 214 extend transversely in opposite directions from the side members 216. The pivot pins 224 are received in a pair of pivot holes 226 formed in a pair of distal fingers 228 on the closure lever plates 154. A jaw closure cable 230 is looped over the bridge pin 218 (FIG. 10) between the side members 216 of the closure control link 214. The closure control link 214 pivots clockwise while the pivot pins 220 slide rearwardly in the guide slots 222 to apply tension to the jaw closure cable 230 when the closure lever plates 154 are actuated by the jaw closure lever 84. At the base of each pivot pin 222 is a raised bearing surface 225 which slides along the inside of the corresponding support plate 122 when the control link 214 is pivoted by the jaw closure plates 154.

Figure 43:
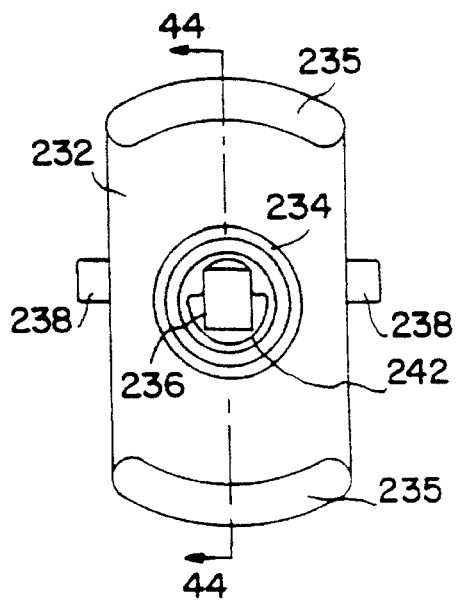
FIG. 43 is an enlarged front view of a stop plate on the actuator handle assembly.
Figure 44:
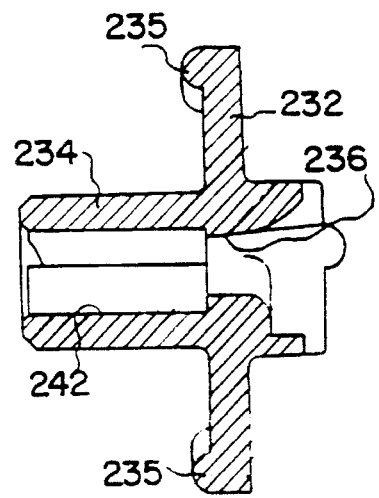
FIG. 44 is a vertical section of the stop plate along line 44—44 of FIG. 43.

The staple firing cable 190 and the jaw closure cable 230 extend through a stop plate 232 located adjacent to the distal end of the support shaft assembly 70. A hollow cylindrical body 234 at the distal end of the stop plate 232 extends into the proximal end of the tubular body 142 of the adjusting nut 140. As shown in FIGS. 43 and 44, a pair of bearing surfaces 235 is formed on the distal side of the stop plate 232 for engaging the semi-circular flanges 106 which form the hub of the control knob 82. The stop plate 232 has a central rectangular slot 236 for receiving the firing cable 190 and the closure cable 230. The stop plate 232 includes a pair of tabs 238 projecting laterally from its opposite sides which are received in a pair of mounting holes 240 (FIG. 14) formed in the support plates 122.

Figure 6:
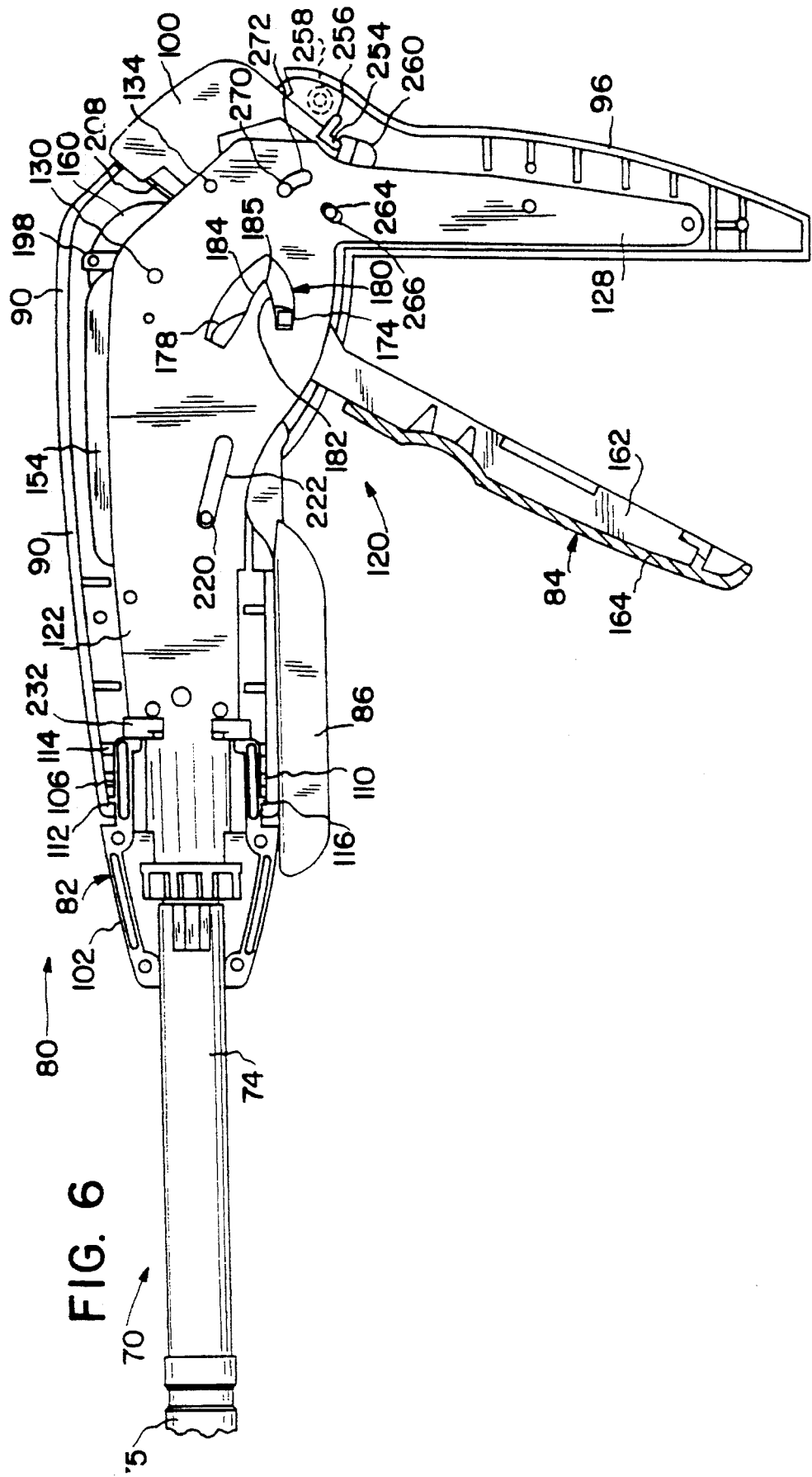
FIG. 6 is a partially cutaway side view of an actuator mechanism contained within the actuator handle assembly of FIG. 2.

Referring to FIGS. 10 and 14, the release button 100 comprises a hollow molded plastic body including a pair of depending flanges 250 on its opposite sides each including a pivot hole 252 for receiving the connecting pin 134 to pivotally mount the release button 100 on the support plates 122. The release button 100 also has a depending rear finger 254 provided with a laterally projecting tab 256 which cooperates with a cylindrical female connector 258 (FIG. 10) on the inside of one of the handle sections 90 and 92 to limit the outward pivotal movement of the release button 100 relative to the actuator handle assembly 80. Pivotally mounted underneath the release button 100 is a release lever 260 which is normally urged by a release spring 262 into engagement with the depending finger 254 of the release button 100. The release lever 260 has a lower pair of pivot pins 264 (one shown) extending transversely in opposite directions therefrom which are received in a pair of pivot holes 266 formed in the support plates 122. As shown in FIG. 6, the pivot holes 266 are enlarged so that the pivot pins 264 are free to slide and pivot relative to the support plates 122. The release lever 260 has a latch arm 268 provided with an upper pair of guide pins 270 extending transversely in opposite directions therefrom which are received in a pair of guide slots 272 formed in the support plates 122. A cam 274 on the underside of the release lever 260 is engaged by the release spring 262 to urge the release lever 260 into engagement with the depending finger 254 of the release button 100. The release spring 262 comprises an elongated flat metal strip which is curled at its opposite ends to form a pair of hollow cylindrical flanges 276 and 278. The lower cylindrical flange 276 is mounted on the lower connecting pin 126. The release spring is flexed about the upper connecting pin 126 and the upper cylindrical flange 278 engages the cam 274 on the release lever 260. The release spring 262 provides a biasing force which urges the release lever 260 against the depending finger 254 to bias the release button 100 in a counter-clockwise direction about the pivot pin 134.

As shown in FIG. 10, each of the closure lever plates 154 has a proximally extending latch lug 280 located adjacent to the release lever 260. When the jaw closure lever 84 is actuated to pivot the closure lever plates 154 about the pivot pin 130 (FIG. 17), the latch lugs 280 engage the arm 268 and pivot the closure lever 260 clockwise against the bias of the release spring 262. When the jaw closure lever 84 is moved to its fully closed position (FIG. 19), the release lever 260 is biased counter-clockwise by the release spring 262 to move the latch arm 268 underneath the latch lugs 280 to latch the jaw closure lever 84 in its fully closed position. The lugs 280 cam against the release lever 260 and the release spring 262 tends to resist the pivotal movement of the closure lever plates 154 relative to the support plates 122 when the jaw closure lever 84 is moved toward its closed position. The camming action of the lugs 280 and the release lever 260 prevents rattling of the actuator mechanism 120 and assists in holding the jaw closure lever 84 in its open position.

Figure 5:
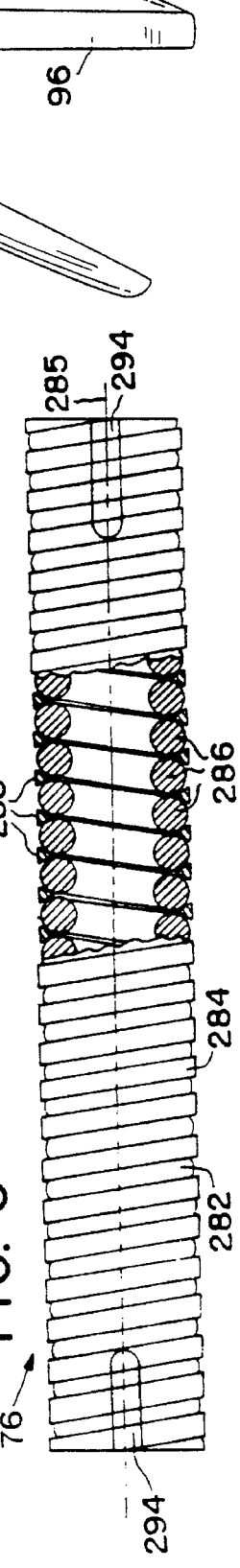
FIG. 5 is an enlarged partially cutaway side elevation showing a flexible section of the support shaft assembly of FIG. 4.
Figure 4:
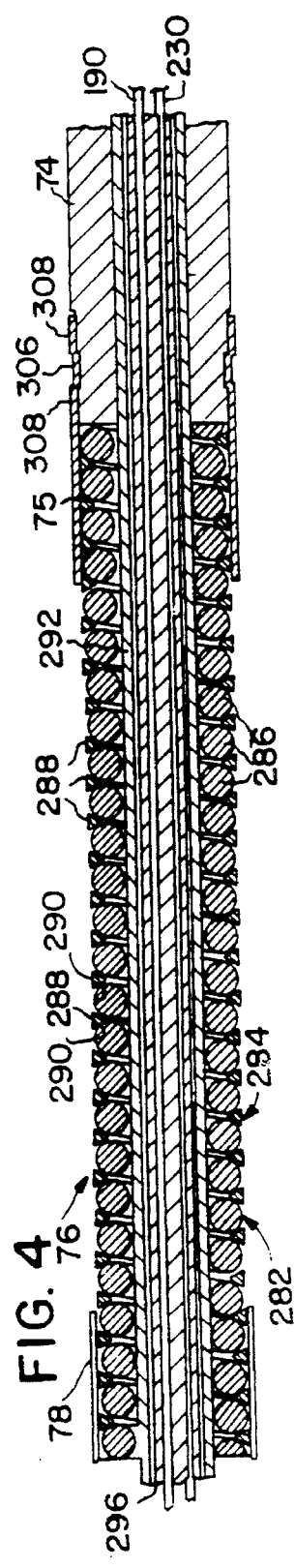
FIG. 4 is an enlarged, partially cutaway longitudinal section of the support shaft assembly of the surgical stapling instrument of FIG. 2.

Referring to FIGS. 4 and 5, the flexible tubular support shaft 76 comprises a dual helical coil structure comprising a first elongated helical member 282 and a second elongated helical member 284 which are concentrically wound together with the coils 286 of the first helical member 282 alternately interspersed with the coils 288 of the second helical member 284. As shown in FIG. 4, each coil 286 of the helical member 282 has a round cross section. Each coil 288 of the helical member 284 has a triangular, wedge-shaped cross section defining a pair of inwardly sloped surfaces 290 which engage the round exterior surfaces of the adjacent round coils 286. The wedge-shaped coils 288 are positioned between the round coils 286 to maintain a desired separation between the adjacent round coils 286 and to maintain the first helical member 282 in tension. The helical coil members 282 and 284, which are preferably made of stainless steel, allow the flexible shaft 76 to be bent in any radial direction relative to the longitudinal axis or centerline 54 (FIG. 3) of the support shaft assembly 70. Inside the helical coil members 282 and 284 is a concentrically mounted cable support tube 292, preferably made of a malleable metal such as aluminum, which allows the flexible shaft 76 to assume its bent or curved shape. The cable support tube 292 is flexible in any radial direction relative to the longitudinal axis or centerline 54 of the support shaft assembly 70. The cable support tube 292 enables the flexible support shaft 76 to assume its curved configuration and to resist tension from the cables 190 and 230 when the stapling head assembly 60 is actuated.

In the preferred embodiment, the flexible support shaft 76 is adapted to be bent within a predetermined range, e.g., up to about ±30° in any direction from its straight configuration. After bending, the flexible support shaft 76 maintains its bent shape (FIG. 3) until the shaft 76 is further manipulated. The malleable cable support tube 292 (FIG. 4) prevents the bent support shaft 76 from inadvertently straightening. This shape retention feature permits access of the stapling head assembly 60 into the pelvic cavity while avoiding contact of the actuator handle assembly 80 with the viscera or body wall. The helical coil members 282 and 284 provide a geometry such that the axis of the shaft assembly 70 remains a substantially constant length during the bending of the flexible support shaft 76. This feature avoids any undesirable change in length which would result in motion of the taut cable system. The twin helical coil construction also provides a solid load path which resists the compressive forces during closure and firing while avoiding any tendency for the flexible support shaft 76 to return to the straight condition.

In addition, the geometry of the circular coils 286 and the triangular coils 288 is such that, at a bending angle of about 30°, one or the other of the coils becomes solid, i.e., either the adjacent round coils 286 engage each other or the adjacent triangular coils 288 engage each other. This condition causes a sharp increase in the force required to bend the flexible support shaft 76 and provides a limit on the extent of the bending motion. This limitation on the angle of bend keeps the cable friction forces low so that the system operates in the regime of substantially constant axis length. The malleable cable support tube 292 is free to slide axially within the helical members 282 and 284 so that any change in the length of the cable support tube 292 due to plastic deformation does not effect thee force required to bend the flexible support shaft 76.

Referring to FIG. 5, in a preferred embodiment of the flexible support shaft 76, the wedge-shaped coils 288 are reduced in width compared with the diameter of the round coils 286. Also, the wedge-shaped coils 288 are shaped to allow the adjacent round coils 286 on the inside of the bend to engage each other when the flexible support shaft 76 is bent to about a 30° bending angle. The helical coil spring member 282 and the helical wrap wire member 284 are coiled together along a common longitudinal axis 285 with the round coils 286 alternating with the triangular or wedge-shaped coils 288 and the coil spring member 282 in tension. The wrap wire member 284 is wrapped about the coil spring member 282 with the wedge-shaped coils 288 positioned between the round coils 286 to maintain a desired separation between the adjacent round coils 286 when the support shaft assembly 76 is straight. The wedge-shaped coils 288 are forced between the adjacent round coils 286 to maintain the coil spring member 282 in tension. The coil spring members 282 and 284 are secured together, e.g., by welding at linear weld areas 294 adjacent to the opposite ends of the flexible support shaft 76. The details of the flexible support shaft 76, the coil spring member 282, the wrap wire member 284, the round coils 286 and the wedge-shaped coils 288 are described in a co-pending U.S. Patent Application entitled "Flexible Support Shaft Assembly" which was filed on Dec. 6, 1993 and assigned to the same assignee, Ethicon, Inc., as the present application. This prior co-pending application is herein incorporated by reference.

Figure 12:
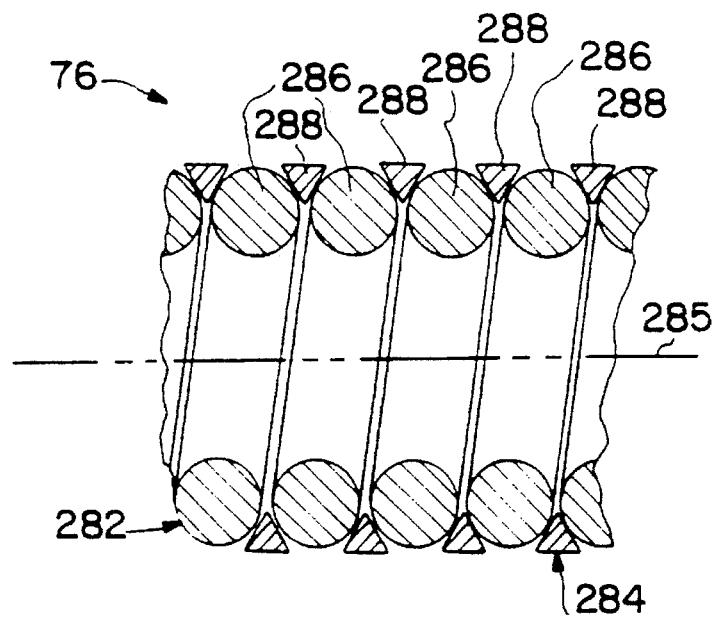
FIG. 12 is an enlarged longitudinal section showing a portion of the flexible support shaft of FIG. 5 in a straight condition.

As shown in FIG. 12, each of the wedge-shaped coils 288 initially separates the adjacent round coils 286 longitudinally from each other when the flexible support shaft 76 is straight. The round coils 286 and the wedge-shaped coils 288 are aligned along the common longitudinal axis 285. The wedge-shaped coils 288 are slidable relative to the round coils 286 to allow the flexible support shaft 76 to bend in a transverse direction relative to its longitudinal axis 285. The sliding action of the wedge-shaped coils 288 allows the flexible support shaft 76 to bend until the round coils 286 on the inside of the bend engage each other and limit the bending of the flexible support shaft 76.

Figure 13:
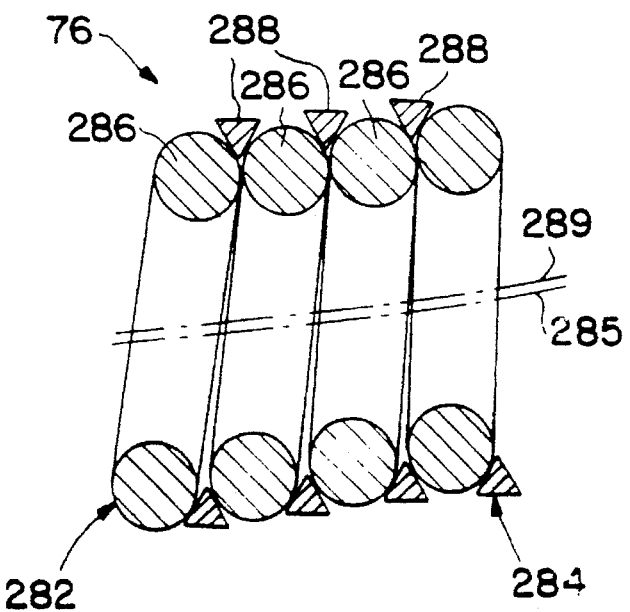
FIG. 13 is an enlarged longitudinal section showing a portion of the flexible support shaft of FIG. 5 in a bent condition.

Referring to FIG. 13, as the flexible support shaft 76 is bent transversely relative to its longitudinal axis 285, the wedge-shaped coils 288 are shifted laterally relative to the adjacent round coils 286. Also, the longitudinal axis 289 of the wedge-shaped coils 288 is shifted slightly relative to the longitudinal axis 285 of the round coils 286 in the direction of the bending of the flexible support shaft 76. The portions of the round coils 286 on the inside of the bend move closer together while the portions of the round coils 286 on the outside of the bend move farther apart. As a result of the sliding action of the wedge-shaped coils 288 relative to the round coils 286, the flexible support shaft 76 is bent into a curved configuration. The bending of the flexible support shaft 76 occurs without any substantial change in the overall length of the flexible support shaft assembly 76 and without stretching of the coil spring member 282 along its axis 285 until the round coils 286 on the inside of the bend move into engagement with each other. Up to this point, the bending of the flexible support shaft 76 can be accomplished by applying a relatively small bending force to the coil spring member 282 and the wrap wire member 284.

After the round coils 286 on the inside of the bend engage each other, a substantially increased bending force must be applied to obtain any further bending of the flexible support shaft 76 in the same direction. Because the portions of the round coils 286 on the inside of the bend are in contact with each other, any additional bending of the flexible support shaft 76 requires the stretching of the coil spring member 282 to move the portions of the round coils 286 on the outside of the bend farther apart. Thus, the point at which the round coils 286 on the inside of the bend move into engagement with each other defines a limit on the bending of the support shaft 76 in the transverse direction.

Figure 11:
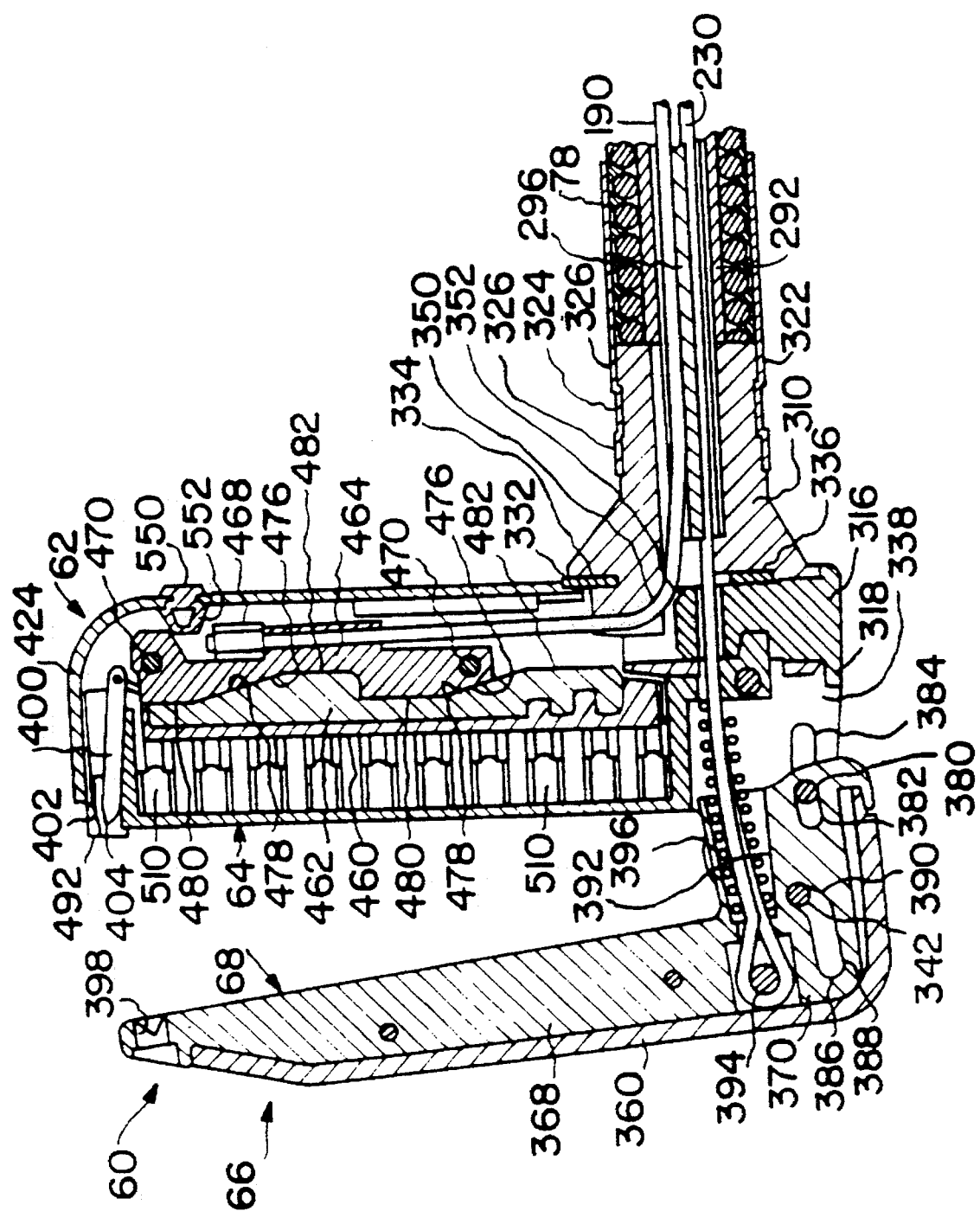
FIG. 11 is an enlarged longitudinal section showing a firing cam mechanism within the stapling head assembly of FIG. 2.
Figure 39:
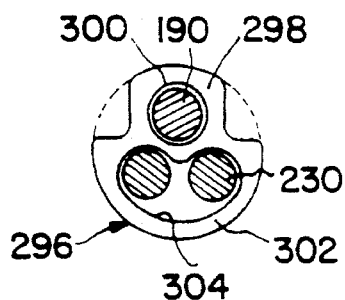
FIG. 39 is an enlarged section of a cable support member in the support shaft assembly.

Referring to FIG. 4, a double lumen cable support member 296 is mounted inside the cable support tube 292. The cable support member 296 extends from the cylindrical body 234 (FIG. 10) of the stop plate 232 to the pivot connection 72 (FIG. 11). As shown in FIG. 39, the cable support member 296 includes an upper section 298 provided with a longitudinal passageway 300 for receiving the staple firing cable 190 and a lower section 302 provided with a longitudinal passageway 304 for receiving the closure cable 230. The lower section 302 has a half-round configuration and the upper section 298 is reduced in width compared with the lower section 302 to define a key-shaped cross section. The stop plate 232 has a key-hole passage 242 (FIG. 43) in its cylindrical body 234 for receiving the key-shaped proximal end of the cable support member 296.

As shown in FIG. 4, the tubular support shaft 74 is secured to the flexible support shaft 76 by the coupling sleeve 75 which is preferably made of a deformable material, e.g., aluminum. The distal end of the tubular support shaft 74 has a series of annular grooves 306 of reduced diameter which provide a series of longitudinally spaced annular ridges 308. The coupling sleeve 75 is deformed, e.g., by magneforming, into contact with the helical coils 286 and 288 and with the annular grooves 306 and annular ridges 308 to secure the coupling sleeve 75 to the tubular support shaft 74 and the flexible support shaft 76. The distal ridge 308 has a pair of flat surfaces 305 (Fig. 15) on its opposite sides to prevent rotation of the tubular support shaft 74 relative to the coupling sleeve 75.

Figure 42:
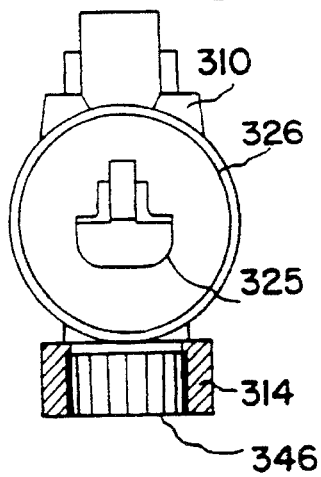
FIG. 42 is an enlarged proximal end view of the pivot connection on the stapling head assembly.

Referring to FIG. 9, the pivot connection 72 which pivotally mounts the stapling head assembly 60 on the shaft assembly 70 comprises a knuckle housing 310 which is mounted on the flexible tubular support shaft 76 by the coupling sleeve 78. The distal end of the flexible support shaft 76 is received in the distal coupling sleeve 78 which is secured, e.g., by magneforming, to the flexible support shaft 76. The knuckle housing 310 includes a pair of hollow, cylindrically shaped hinge arms 312 and 314 (FIG. 16) which receive a cylindrical knuckle pin 316 for rotation in a hinge-like fashion. A distally projecting flange 318 is formed at the bottom of the knuckle pin 316. A passage 320 (FIG. 33) extends radially through the knuckle pin 316 for slidably receiving the closure cable 230. The knuckle housing 310 and the knuckle pin 316 are preferably made of plastic material. The knuckle housing 310 includes a hollow cylindrical body 322 projecting distally therefrom and received in the coupling sleeve 78 which is preferably made of aluminum. The cylindrical body 322 has an annular groove 324 on its outer surface which provides a pair of longitudinally spaced annular ridges 326. The coupling sleeve 78 is deformed, e.g., by magneforming, into contact with the annular groove 324 and annular ridges 326 and with the helical coils 286 and 288 to secure the knuckle housing 310 to the flexible support shaft 76. The proximal ridge 326 has a pair of flat surfaces 315 (Figure 16) on its opposite sides to prevent rotation of the knuckle housing 310 relative to the flexible support shaft 76. The cylindrical body 322 has a longitudinal key-hole passage 325 (FIG. 42) for receiving the distal key-shaped end of the cable support member 296.

As shown in FIG. 7, the fixed jaw 62 includes a head plate 328, preferably made of metal, e.g., stainless steel, which is adapted to receive and support the staple cartridge 64. The head plate 328 (FIG. 16) is formed as a double-walled, generally rectangular member with a pair of opposed vertical side walls 330 which are mirror images of each other. The staple cartridge 64, preferably made of plastic material, has a narrow rectangular configuration and is mounted at the front of the head plate 328 between the side walls 330.

As shown in FIG. 7, the head plate 328 is pivotally supported by the knuckle housing 310 and the knuckle pin 316. The side walls 330 are joined together by an upper flange 332 which is curved and slidably received in an arcuate channel 334 (FIG. 11) formed at the top of the knuckle housing 310. The side walls 330 are also joined together by a lower flange 336 which is curved and rotatably received behind the knuckle pin 316 between the hinge arms 312 and 314. With the knuckle pin 316 inserted into the cylindrical flanges 312 and 314, the head plate 328 is attached to the knuckle housing 310 in a hinge-like manner to pivotally support the stapling head assembly 60 at the distal end of the support shaft assembly 70. The side walls 330 of the head plate 328 include a pair of distally projecting side plates 338 which are spaced apart and provided with holes 340 for receiving a bearing pin 342. The lower flange 318 on the knuckle pin 316 is received between the side plates 338.

Figure 16:
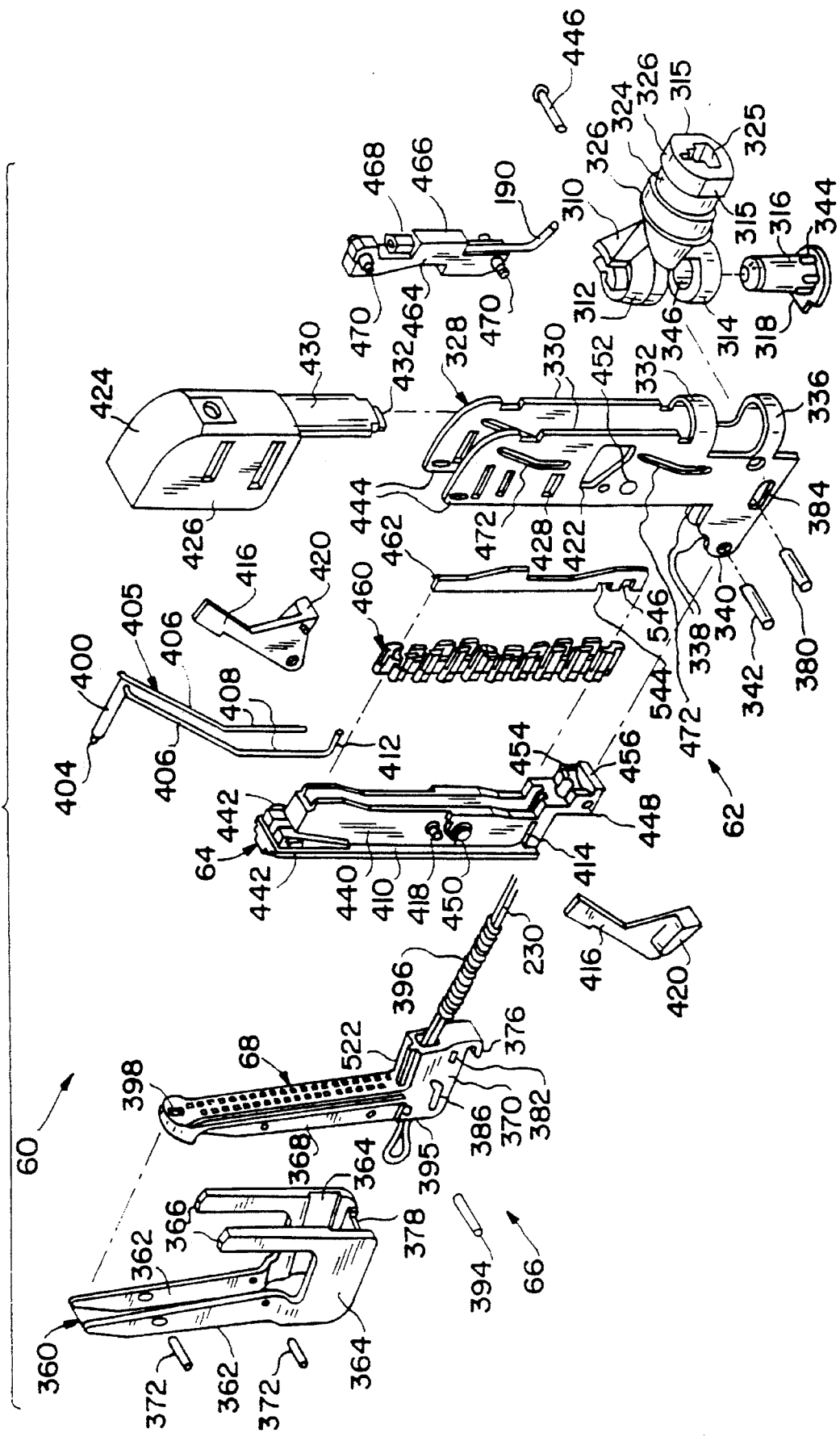
FIG. 16 is an exploded perspective view of the components of the stapling head assembly.

Referring to FIG. 16, the knuckle pin 316 has a set of detents 344 at its lower end which cooperate with a series of circumferentially spaced notches 346 formed on the interior of the lower hinge arm 314 to provide a detent mechanism for controlling the pivotal movement of the knuckle pin 316 relative to the knuckle housing 310. There are six detents 344 (FIG. 32) at the bottom of the knuckle pin 316 which are uniformly spaced 60° apart. The six detents 344 cooperate with eighteen notches 346 (FIG. 42) which are uniformly spaced apart by 20° on the inside of the lower hinge arm 314. The detents 344 on the knuckle pin 316 engage the notches 346 on the interior of the lower hinge arm 314 to define 20° intervals for the pivotal movement of the stapling head assembly 60 about the vertical axis 52. The detents 334 and notches 346 allow the stapling head assembly 60 to pivot over a range of about ±80° relative to the longitudinal axis 54.

As shown in FIG. 11, the knuckle housing 310 is provided with an upwardly curved cable passage 350 for receiving the firing cable 190. The curved passage 350 in the knuckle housing 310 allows the firing cable 190 to turn smoothly at right angles as it passes through the knuckle housing 310. The top of the knuckle pin 316 has a conical surface 352 (FIG. 32) which extends circumferentially about the knuckle pin 316 and provides a clearance for the firing cable 190 and allows the knuckle pin 316 to rotate about its axis without interference with the firing cable 190.

Referring to FIGS. 32–34, the cable passage 320 in the knuckle pin 316 is oval in shape for receiving the closure cable 230. The cable passage 320 has opposite inner walls 354 (FIG. 34) which curve outwardly in the proximal direction so that the cable passage 320 terminates at a rearwardly facing slot 356 (FIGS. 32–33) on the proximal side of the knuckle pin 316. As shown in FIG. 34, the oppositely curved walls 354 of the passage 320 provide a path of substantially constant length for the closure cable 230 as the knuckle pin 316 is rotated relative to the knuckle housing 310. This constant length feature tends to prevent changes in the tension on thee closure cable 230 and changes in the gap between the staple cartridge 64 and the anvil 68 when the stapling head assembly 60 is rotated about the vertical axis 52 relative to the support shaft 70.

Referring to FIG. 16, the movable jaw 66 comprises a generally L-shaped anvil shroud 360, preferably made of molded plastic material, including a pair of elongated vertical flanges 362 extending upwardly from a pair of side plates 364. A cam actuator finger 366 projects upwardly at the rear of each side plate 364. The staple forming anvil 68 comprises a generally L-shaped member, preferably made of metal, e.g., aluminum, including an elongated upstanding distal arm 368 which projects upwardly from a rectangular base member 370. The distal arm 368 of the anvil 68 is received between and secured to the vertical flanges 362 by a pair of spring pins 372. The anvil 68 has a pair of elongated flanges 374 extending along the opposite sides of its arm 368 which engage the vertical flanges 362 of the anvil shroud 360. The proximal edges of the elongated flanges 374 serve as cutting guides for a surgical knife or scalpel. A depending curved finger 376 is formed at the proximal end of the base member 370 and is received in a corresponding notch 378 formed at the bottom of the anvil shroud 360.

As shown in FIG. 16, the movable jaw 66 is slidably and pivotally mounted on the fixed jaw 62 in the following manner. A slide pin 380 is slidably received in an elongated horizontal slot 382 formed in the base member 370 of the anvil 68. The opposite ends of the slide pins 380 are slidably received in a pair of elongated horizontal slots 384 formed in the side plates 338 of the head plate 328. The slide pin 380 which is slidable within the slots 382 and 384 pivotally supports the base member 370 of the anvil 68 on the head plate 328 and allows the movable jaw 66 to slide and pivot into a closed position relative to the fixed jaw 62. The outer ends of the bearing pin 342 are inserted into the holes 340 of the side plates 338. The bearing pin 342 is slidably received in an elongated guide slot 386 formed in the base member 370 of the anvil 68. The guide slot 386 includes a longitudinal section 388 and an upwardly inclined section 390 (FIG. 11). The bearing pin 342 and the guide slot 386 guide the movable jaw 66 into an upright position adjacent to the fixed jaw 62 when the stapling head assembly 60 is closed.

As shown in FIGS. 11 and 16, a closure cable passageway 392 extends longitudinally through the base member 370 of the anvil 68. The closure cable 230 comprises a continuous flexible belt with loops at its opposite ends. The closure cable 230 extends into the passageway 392 and is looped over a closure cable pin 394 inserted in a pair of holes 395 (one shown) extending into the opposite sides of the base member 370 and intersecting the cable passageway 392. When the distal arm 368 of the anvil 68 is inserted into the anvil shroud 360, the cable closure pin 394 is retained in the holes 395 by the vertical flanges 362 of the anvil shroud 360. Similarly, when the anvil 68 and the anvil shroud 360 are assembled with the head plate 328, the bearing pin 342 is retained in the holes 340 and the slide pin 380 is retained in the slots 384 of the side plates 338 by the side plates 364 of the anvil shroud 360. The closure cable 230 extends through a compression return spring 396 which extends into the cable passageway 392. The compression return spring 396 is engaged with the base member 370 inside the passageway 392 and with the staple cartridge 64 to normally bias the movable jaw 66 to the open position.

Referring to FIG. 11, a passage 398 extends longitudinally through the tip of the anvil 68 on the movable jaw 66. A retractable tissue retaining pin 400 mounted on the fixed jaw 62 is extended through a passage 402 in the staple cartridge 64 into the passage 398 when the movable jaw 66 is closed. The tissue retaining pin 400 comprises an elongated cylindrical member, preferably made of metal, e.g., stainless steel, with a rounded or pointed distal end 404. The tissue retaining pin 400 is pivotally attached to an elongated U-shaped wire spring 405 (FIG. 16) which extends through a pivot hole at the proximal end of the pin 400. The spring 405 has a pair of cantilever spring arms 406 which span the staple cartridge 64. The spring arms 406 terminate in a pair of vertical members 408 which are inserted into a pair of slots 410 formed on opposite sides of the staple cartridge 64. One of the vertical spring members 408 has a curved end 412 which is inserted into a curved slot 414 on one side of the staple cartridge 64.

A pair of pin placement arms 416 is pivotally mounted on a pair of laterally projecting pivot pins 418 on opposite sides of the staple cartridge 64. The pin placement arms 416 are positioned to engage the cantilever spring arms 406 of the tissue retainer spring 405. Each pin placement arm 416 includes a wedge-shaped cam 420 which projects laterally outward from a window 422 formed in each of the side walls 330 of the head plate 328. When the movable jaw 66 is closed, the cam actuator fingers 366 engage the cams 420 to pivot the pin placement arms 416 counter-clockwise, as viewed in FIG. 9, to advance the tissue retaining pin 400 from the fixed jaw member 62 into the passage 398 formed at the tip of the anvil 68 to capture the tissue between the anvil 68 and the staple cartridge 64. When the movable jaw member 66 is opened, the cantilever spring arms 406 retract the tissue retaining pin 400 into the fixed jaw member 62. Also, the compression spring 396 returns the movable jaw member 66 to its open position.

As shown in FIG. 16, a hollow plastic cover 424 is fitted over the top portions of the side walls 330 of the head plate 328. The cover 424 has a pair of forward projecting side flaps 426 which provide an earmuff-like shield over the top portions of the side plates 330. Each of the side flaps 426 includes a pair of internal ribs (not shown) which are received in a pair of longitudinal slots 428 formed in each of the side plates 330 to fasten the cover 424 on the head plate 328. The cover 424 also includes a depending proximal arm 430 provided with a tab 432 at its lower end which is received inside the upper curved flange 332 of the head plate 328.

Referring to FIG. 16, the staple cartridge 64 comprises an elongated, generally rectangular housing 440, preferably made of plastic, which is received between the side plates 330 of the head plate 328. A pair of fastener pins 442 projecting laterally from opposite sides at the top of the staple cartridge 64 are received in a pair of vertical slots 444 formed in the side walls 330 of the head plate 328. The staple cartridge 64 is secured to the side walls 330 by a rivet 446 which extends transversely through the depending leg 448 at the bottom of the staple cartridge 64. A pair of cylindrical locator pins 450 on opposite sides of the staple cartridge 64 is received in a pair of openings 452 formed in the side walls 330 of the head plate 328. The depending leg 448 has a curved bearing surface 454 for engaging the cylindrical knuckle pin 316. Also, a horizontal flange 356 at the base of the depending leg 448 is received in a notch 458 (FIG. 32) formed at the front of the cylindrical knuckle pin 316.

Referring to FIG. 11, a staple driver 460 is slidably mounted in the staple cartridge 64 for driving the staples 65 against the anvil 68. The staple driver 460 is preferably made of plastic material and includes an insert 462 made of metal, e.g., stainless steel, which reinforces the plastic staple driver 460 to resist the forces encountered when the staples 65 are formed. The staple driver 460 is actuated by a slidable firing cam 464 made of metal, e.g., stainless steel, which is slidably mounted on the fixed jaw 62 and engaged with the staple driver insert 462. The firing cam 464 includes a proximal offset section 466 provided with a longitudinal bore in which the firing cable 190 is inserted. A cable crimp member 468 which is hexagonal in shape is secured to the distal end of the firing cable 190 to actuate the firing cam 464 when the firing cable 190 is pulled in the proximal direction.

The firing cam 464 forms part of a dual cam actuator mechanism for actuating the staple driver 460 with different mechanical advantages when the staple firing trigger 86 is actuated. The dual cam actuator mechanism is adapted to actuate the staple driver 460 with a first mechanical advantage over a first portion of the stroke of the staple firing trigger 86 and with a second mechanical advantage over a second portion of the stroke of the staple firing trigger 86.

As shown in FIG. 16, the firing cam 464 includes a pair of laterally projecting pins 470 on each of its sides which are slidably received in a pair of inclined cam slots 472 formed in each of the side walls 330 of the head plate 328. The pins 470 and cam slots 472 provide a first portion of the dual cam mechanism for actuating the staple driver 460. Each cam slot 472 is inclined downwardly toward the front of the head plate 328, e.g., at an angle of 15° from the vertical axis 52 (FIG. 1). As the firing cam 464 is pulled downwardly by the firing cable 190, the pins 470 ride along the inclined slots 472 so that the firing cam 464 and the staple driver 460 are displaced in the distal direction. Each of the cam slots 472 terminates in a bottom portion 474 which is angled slightly backward on the head plate 328 to reduce the load encountered in the over-travel operation which is described below.

Referring to FIG. 11, the firing cam 464 is contoured at its distal edge to provide a pair of inclined cam actuator surfaces 476 which slidably engage a complementary pair of inclined cam follower surfaces 478 formed at the proximal edge of the staple driver insert 462. The cam actuator surfaces 476 and the cam follower surfaces 478 provide a second portion of the dual cam mechanism for actuating the staple driver 460. Preferably, both pairs of inclined cam surfaces 476 and 478 are inclined at an angle of 15° from the vertical axis 52. Each inclined cam actuator surface 476 on the firing cam 464 terminates in a flat cam actuator surface 480 oriented parallel to the vertical axis 52. Similarly, each inclined cam follower surface 478 on the staple driver 460 terminates in a flat cam follower surface 482 oriented parallel to the vertical axis 52. As the firing cam 464 is pulled downwardly by the firing cable 190, the inclined cam surfaces 476 on the firing cam 464 ride along the inclined cam surfaces 478 on the staple driver insert 462 to push the staple driver 460 distally relative to the firing cam 464. The flat cam surfaces 480 on the firing cam 464 are arranged to engage the flat cam surfaces 482 on the staple driver insert 462 before the pins 470 on the firing cam 464 arrive at the bottom vertical portions 474 of the inclined slots 472. When the firing cam 464 is actuated, the first cam mechanism provided by the inclined cam surfaces 476 and 478 bottoms out before the second cam mechanism provided by the pins 470 and inclined slots 472.

The dual cam mechanism of the stapling head assembly 60 occupies less space than the staple firing mechanisms of the prior art. Thus, the outer dimensions of the fixed jaw 62 which houses the dual cam mechanism are minimized to allow the stapling head assembly 60 to access restricted surgical sites, e.g., in the pelvic area.

Generally, the surgical stapling instrument 50 is operated in the following manner. With the jaws 62 and 66 open, the stapling head assembly 60 is articulated about the vertical axis 52 to a desired angular position relative to the longitudinal axis 54. The flexible tubular shaft 76 is bent into a curved configuration to conform to the anatomy of the patient. By rotation of the control knob 82, the shaft assembly 70 can be rotated about its longitudinal axis 54 to orient the actuator handle assembly 80 in a comfortable position for actuation by the surgeon.

Next, by manipulating the surgical stapling instrument 50 after insertion into a body cavity, the stapling head assembly 60 is positioned inside the body and a tissue lumen 55 (FIG. 7) to be stapled is located in between the open stapler jaws 62 and 66. The movable jaw 66 is partially closed by actuating the jaw closure lever 84 with one hand. The tissue retaining pin 400 is advanced from the fixed jaw 62 into engagement with the movable jaw 66 to capture the lumen 55 (FIG. 18) between the jaws 62 and 66. The other hand is used to guide the stapling head assembly 60 into the desired position. With the jaw closure lever 84 in the partially closed position, the stapling head assembly 60 can be moved along the captured lumen 55 to the desired stapling position. If desired, the jaw closure lever 84 can be returned to its inoperative position to return the movable jaw 66 to its fully open position and to retract the tissue retaining pin 400 into the fixed jaw 62 to allow the stapling instrument 50 to be withdrawn from the body cavity for adjustment of the articulation of the stapling head assembly 60 and the curvature of the flexible tubular shaft 76.

When the stapling head assembly 60 is located in the desired stapling position on the lumen 55, the jaw closure lever 84 is moved to its fully clamped position (FIG. 19) to completely close the jaw 66 to clamp the lumen 55 between the staple cartridge 64 and the anvil 68. Next, the firing trigger 86 is grasped and squeezed to fire the staples 65 in the staple cartridge 64. As shown in FIG. 22, the staples 65 are advanced into engagement with the anvil 68 and are formed into a B-shaped configuration to staple the tissue lumen 55 together. The lumen 55 is transected by using right angle scissors or by running a scalpel along the cutting guides formed by the longitudinal flanges 374 at the edges of the staple cartridge 64 or the anvil 68. The jaws 62 and 66 are unclamped from the lumen 55 by squeezing both levers 84 and 86 toward the handle grip 96 and depressing the release button 100 to actuate the release lever 260 to unlatch the jaw closure lever 84. With the jaws 62 and 64 unclamped and the tissue retaining pin 400 retracted, the stapling instrument 50 is removed from the body cavity.

Initially, with the jaw closure lever 84 in its open position (FIG. 10), the staple firing lever 86 is located at an open and unfired position adjacent to the body of the actuator handle assembly 80. The drive gears 194 are oriented with the drive lugs 196 rotated in a counter-clockwise direction away from the side lugs 198 on the pulley 160. The detents 206 on the pulley 160 are engaged by the anti-backup tang 208 on the release button 100 to stop the rotation of the pulley 160 in a first position and prevent the pay-out of the firing cable 190 before the staple firing lever 86 is actuated. The pulley 160 is held against counter-clockwise rotation by the anti-backup tang 208 and a slight tension is maintained in the firing cable 190. Also, at the initial position of the pulley 160, the firing cable 190 is engaged by the first cam lobe region 210 (FIG. 38).

When the jaw closure lever 84 is actuated, i.e., pivoted in a counter-clockwise direction about the pivot pin 130, each firing lever guide pin 174 travels rearward along the lower cam track section 182 of the cam slot 180 and causes the firing lever 86 to rotate in a counter-clockwise direction about the pivot pins 168 and downward relative to the body of the actuator handle assembly 80 into a ready to fire position. The pivotal motion of the firing lever 86 and the jaw closure lever 84 causes the drive gears 194 to rotate clockwise to advance the drive lugs 196 into engagement with the side lugs 198 on the pulley 160. Initially, the jaw closure lever 84 is moved to a partially closed position (FIG. 17) in which the staple firing lever 86 is pivoted slightly downward from the body of the actuator handle assembly 80. Also, the movement of the jaw closure 84 to the detent position causes the control link 214 to slide and pivot on the pivot pins 220 which travel rearwardly along the guide slots 222. The control link 214 applies tension to the closure cable 230 to pull the distal jaw 66 into an upright, partially closed position (FIG. 18).

Referring to FIG. 17, as the jaw closure lever 84 is moved toward its closed position, each of the latch lugs 280 on the closure lever plates 154 pushes against the latch arm 268 on the release lever 260 which pivots in a clockwise direction about its pivot pins 264 to allow the latch lugs 280 to move above the release lever 260. The guide pins 270 at the top of the arm 268 slide along the guide slots 272 to permit the pivotal movement of the release lever 260. When the jaw closure lever 84 is moved to the closed and ready to fire position (FIG. 19), the latch lugs 280 are located above the latch arm 268 and the release lever 260 is biased in a counter-clockwise direction by the release spring 262 to latch the closure lever plates 154 and the jaw closure lever 84 in the closed and ready to fire position.

Referring to FIGS. 1 and 14, during the closure of the stapling instrument 50 by actuation of the jaw closure lever 84, the forces applied by hand to the depending lever portions 162 of the closure lever plates 154 are transmitted by the fingers 228 and the closure control link 214 to the closure cable 230. The closure control link 214 pivots in a counter-clockwise direction about the pins 220 which slide rearwardly along the guide slots 222. The tension applied to the closure cable 230 by the closure control link 214 is transmitted via the closure cable pin 394 to the anvil 68 to pull the movable jaw 66 toward the fixed jaw 62. Initially, the movable jaw 66 is pivoted about the slide pin 380 into an upright position (FIG. 18). The base member 370 of the anvil 68 is guided in movement relative to the base plates 338 by the slide pin 380 which travels along the slots 382 and 384 and by the bearing pin 342 which travels along the inclined portion 390 of the guide slot 386.

As the movable jaw 66 is pivoted into the upright position, the cam fingers 366 engage the corresponding cams 420 and pivot the pin placement arms 416 counter-clockwise, as viewed in FIG. 9, about the pivot pins 418. The pin placement arms 416 bend the cantilever spring arms 406 forward to extend the tip portion 404 of the tissue retaining pin 400 through the passage 402 at the top of the staple cartridge 64 and into the passage 398 at the top of the anvil 68. At this point, as shown in FIG. 18, the bearing pin 342 is positioned at the juncture between the longitudinal portion 388 and the inclined portion 390 of the guide slot 386 and the movable jaw 66 is upright.

Figure 19:
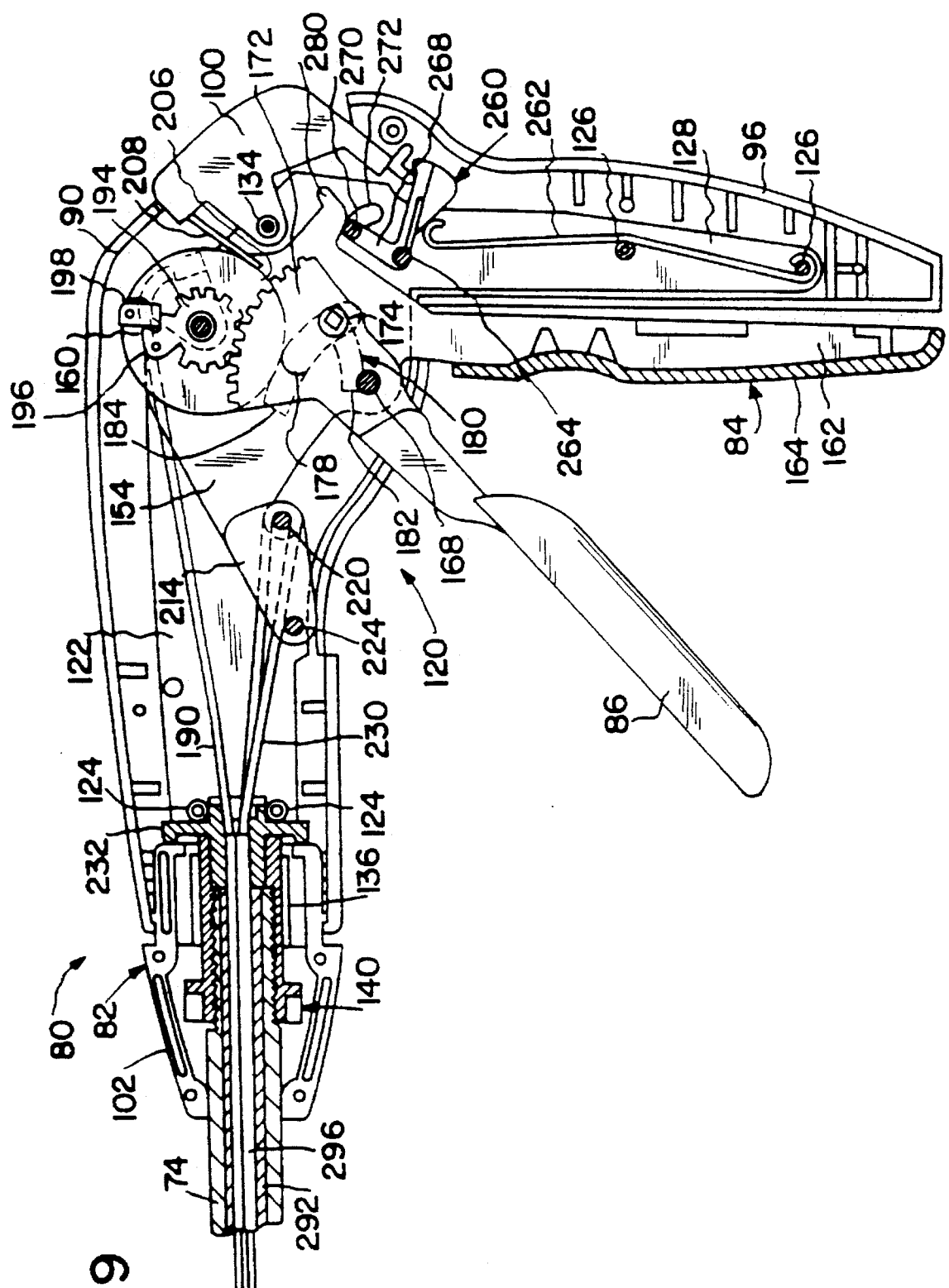
FIG. 19 is a partially cutaway side view showing the actuator mechanism in a closed and ready to fire position.

After the movable jaw 66 is pivoted into the upright position, the bearing pin 342 is slidably received in the longitudinal portion 388 of the guide slot 386 to allow the anvil base 370 to slide longitudinally relative to the fixed jaw 62. Next, as shown in FIG. 19, the jaw closure lever 84 is moved to its fully closed position adjacent to the depending handle grips 96 of the actuator handle assembly 80. The closure control link 214 is pivoted in a counter-clockwise direction and the pins 220 travel rearwardly along the guide slots 222. As the movable jaw 66 is pulled closer toward the fixed jaw 62 (FIG. 20), the tip of the anvil 68 moves into engagement with a tissue stop 492 at the top of the staple cartridge 64. Thereafter, the movable jaw 66 pivots slightly about the tissue stop 492 until the bearing pin 342 is engaged by the distal ends of the guide slot 386 (FIG. 20). This bottoming out point occurs before the jaw closure lever 84 reaches the end of its travel. As the jaw closure lever 84 completes its stroke, the high mechanical advantage of the over-center control link 214 stretches the closure cable 230 and applies a high force, approximately 200 pounds, to pre-load the stapling jaw assembly 60 into the closed position. This high pre-load force helps to resist the staple forming forces encountered during the firing of the staples 65 in the staple cartridge 64.

During the motion of the jaw closure lever 84, the staple firing lever 86 is deployed from an inoperative position (FIG. 10) underneath the body of the actuator handle assembly 80 into an intermediate firing position (FIG. 19) so that the staple firing lever 86 can be grasped by the surgeon for firing of the stapling instrument 50. The pivot axis for the staple firing lever 86 is provided by the pivot pins 168 which are received in the pivot holes 170 formed in the closure lever plates 154. As the jaw closure lever 84 is drawn backward, the staple firing lever 86 is carried backward with the jaw closure lever 84 and the deployment pins 174 travel along the cam slots 180 formed in the support plates 122.

Initially, as shown in FIG. 17, each of the deployment pins 174 moves along the upwardly and rearwardly curved cam track section 182 of the corresponding cam slot 180. Also, the deployment pins 174 travel partially along the arc-shaped slots 178 in the closure lever plates 154. The movement of each deployment pin 174 along the corresponding lower cam track section 182 forces the staple firing lever 86 to rotate about the pivot pin 168 and deploys the staple firing lever 86 in its firing position at an angle of about 45° from its horizontal start position. As the staple firing lever 86 is deployed in its firing position, the gear sectors 172 on the staple firing lever 86 rotate the drive gears 194 in a clockwise direction to advance the drive lugs 196 toward the side lugs 198 on the pulley 160. As long as each deployment pin 174 is located in the corresponding inclined cam track section 182, the movement of the jaw closure lever 84 can be reversed to return the staple firing lever 86 to its substantially horizontal position.

During the deployment of the staple firing lever 86, the movement of the staple firing lever 86 relative to the jaw closure plates 154 is restricted by the deployment pins 174 which are confined in the lower cam track sections 182. Thus, any manual pulling force applied to the staple firing lever 86 during its deployment merely urges the jaw closure lever 84 toward its closed position. Since the deployment pins 174 are confined in the lower cam track sections 182, the staple firing lever 86 cannot be actuated to fire the staples in the staple cartridge 64. When the jaw closure lever 84 is pulled to its fully closed position, each of the pivot pins 220 is located at the proximal end of the corresponding guide slot 222 and each of the deployment pins 174 is located at a rear corner 185 of the corresponding cam slot 180 where the curved cam track sections 182 and 184 intersect. At this point, the arc-shaped slot 178 of each jaw closure plate 154 is aligned with the upper curved cam track section 184 of the corresponding cam slot 180 and the staple firing lever 86 is free to pivot relative to the jaw closure lever 84 to actuate the stapling head assembly 60.

When the jaw closure lever 84 arrives at its fully closed position (FIG. 19), the drive lugs 196 on the gears 194 engage the side lugs 198 on the pulley 160. The drive gears 194 are ready to actuate the pulley 160 and the firing cable 190. At this point, the pulley 160 is latched in an unfired position by the anti-backup tang 208 on the release button 100 which engages the peripheral teeth 206 on the pulley 160. Also, as the jaw closure lever 84 is moved to its closed position, the lugs 280 on the jaw closure plates 154 push against the latch arm 268 to pivot the release lever 260 in a clockwise direction about its pivot pins 264 against the bias of the release spring 262. After the jaw closure lever 84 is moved to its closed position, the release lever 260 is biased in a counter-clockwise direction by the release spring 262 to move the latch arm 268 underneath the lugs 280 of the jaw closure plates 154 to latch the jaw closure arm 84 in the closed position.

Next, the staple firing lever 86 is grasped and pulled toward the jaw closure lever 84. The staple firing lever 86 is pivoted about the pivot pins 168 in a counter-clockwise direction toward its fired position (FIG. 21). The arc-shaped slots 178 in the jaw closure plates 154 are aligned with the upper curved cam track sections 184 of the cam slots 180 in the support plates 122. The deployment pins 174 are free to travel along the upper curved cam track sections 184 to allow the staple firing lever 86 to pivot to its fired position to actuate the stapling head assembly 60. Also, when the staple firing lever 86 is moved to its fired position, the deployment pins 174 travel to the upper distal ends of the arc-shaped slots 178. As the staple firing lever 86 is pivoted toward its fired position, the drive gears 194 are rotated in a counter-clockwise direction by the gear sectors 172. The drive lugs 196 engage the side lugs 198 and rotate the pulley 160 in a counter-clockwise direction to apply tension to the firing cable 190 to actuate the firing cam 464 in the stapling head assembly 60. The firing of the staples in the staple cartridge 64 is explained in more detail below. With the staple firing lever 86 in its fired position, the pulley 160 is rotated to its fired position in which the anti-backup tang 208 engages the peripheral teeth 209 (FIG. 35) to latch the pulley 160 in its fired position and to prevent the payout of the firing cable 190.

The stapling head assembly 60 is re-opened after the firing of the staples 65 by squeezing the staple firing lever 86 and the jaw closure lever 84 toward the depending handle grips 96 and depressing the release button 100 to pivot the release lever arm 260 in a clockwise direction about the pivot pins 264. The jaw closure plates 154 are pivoted counter-clockwise to an over-travel position (FIG. 23) to raise the latch lugs 280 slightly relative to the latch arm 268 to allow the release lever 260 to be pivoted clockwise by contact with the rear finger 254 of the release button 100. When the gripping pressure on the firing lever 86 and the jaw closure lever 84 is relaxed, the distal jaw 66 is pushed away from the proximal jaw 62 by the compression return spring 396 which draws the closure cable 230 in the distal direction (FIG. 25). As a result, each of the control link pivot pins 220 slides forward in the corresponding guide slot 222 and the control link 214 pivots in a clockwise direction to pivot each closure lever plate 154 clockwise about the pivot pin 130 to return the jaw closure lever 84 to its open position (FIG. 24). The staple firing lever 86 remains in a fired position adjacent to the jaw closure lever 84 when the stapling head assembly is opened. The deployment pins 174 remain in the upper curved cam track sections 184 to prevent the staple firing lever 86 from returning to its horizontal start position. With the stapling head assembly 60 open, the control link 214 is returned to its initial position and each pivot pin 220 is returned to the distal end of the corresponding guide slot 222.

Because of the substantial opening loads on the closure lever plates 154 during the initial stage of the re-opening, the staple firing lever 86 is held against the jaw closure lever 84 and the firing lever guide pin 174 remains in the upper cam track 184 of the firing lever guide slot 180. Initially, the pulley 160 rotates in a clockwise or firing direction to increase the tension in the firing cable 190. The tension in the firing cable 190 causes the firing lever 86 to separate slightly from the jaw closure lever 84. The separation of the staple firing lever 86 from the jaw closure lever 84 allows the pulley 160 to rotate slightly in a counter-clockwise direction to pay out the firing cable 190. As a result of the pay-out of the firing cable 190, the tension in the firing cable 190 decreases to allow the jaw closure lever 84 to freely return to its open position. The pulley 160 is rotated in the counter-clockwise direction until the anti-backup tang 208 engages the detents 206 to stop the rotation of the pulley 160 so that the tension in the firing cable 190 no longer tends to further open the firing lever 86. In the fully re-opened position, the motion of the firing lever guide pin 174 is restricted by the upper cam track 184 of the firing lever guide slot 180 to prevent the firing lever 86 from returning to its original position adjacent to the body of the actuator handle assembly 80.

In the actuation of the stapling head assembly 60, the firing cam 464 is pulled downwardly by the firing cable 190 and the staple driver 460 is advanced by two cam mechanisms. First, the firing cam pins 470 travel in the firing cam slots 472 which are inclined downwardly and forwardly at an angle of 15° relative to the vertical axis 52. Second, the inclined cam surfaces 476 and 478 on the firing cam 464 and the staple driver 460, respectively, engage each other and result in further displacement of the staple driver as the firing cam 464 is pulled downwardly. This dual cam mechanism achieves a high mechanical advantage in a compact space. The geometry of the two cam mechanisms is such that the firing cam 464 and the staple driver insert 462 move into engagement at the flat cam surfaces 482 and 480 before the travel of the firing cam pins 470 in the firing cam slots 472 is completed. This arrangement allows the staple driving mechanism to operate with two mechanical advantages, i.e, a low mechanical advantage during the initial stroke when both cam mechanisms are engaged and a high mechanical advantage toward the end of the stroke when only the firing cam slots 472 are engaged. The changeover in the operation of the dual cam mechanisms occurs at a low point in the forming force deflection curve for the staples. This operation effectively minimizes the firing cable force at all points in the firing stroke of the staple forming mechanism.

Figure 26:
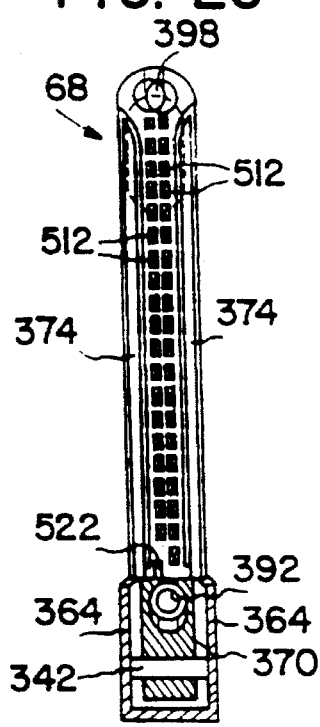
FIG. 26 is an enlarged, partially cutaway proximal view of the anvil on the movable jaw of the stapling head assembly.

Referring to FIG. 11, the staple cartridge 64 includes a plurality of staple receiving slots or pockets 510 which are formed in the housing 440 and arranged in one or more longitudinal rows. Preferably, the staple receiving pockets 510 are arranged in two longitudinal rows (FIG. 27) so that the rows of staples 65 are staggered relative to each other. As shown in FIG. 26, the anvil 68 includes a pair of longitudinally extending rows of staple forming grooves 512 which are arranged in pairs aligned with the staple receiving pockets 510 in the staple cartridge 64. The grooves 512 form the staples 65 into a B-shaped configuration when the staple driver 460 is advanced to drive the staples 65 against the anvil 68.

Figure 27:
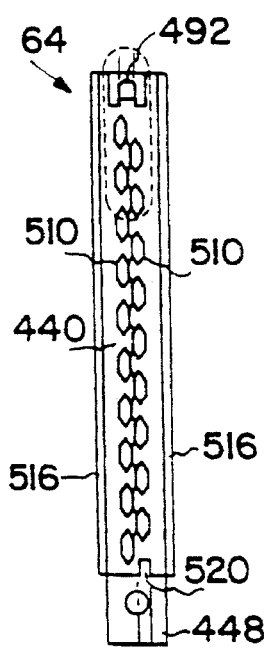
FIG. 27 is an enlarged, partially cutaway distal view of the staple cartridge on the fixed jaw of the stapling head assembly.

In the embodiment of the staple cartridge 64 shown in FIG. 27, the right-hand row has nine staple receiving pockets 510 and the left-hand row has ten pockets 510. It will be understood by persons skilled in the art that other arrangements of staple receiving pockets 510 can be employed. For example, the staple cartridge 64 may include a single row of staple receiving pockets 510, or three or more staggered rows of staple receiving pockets 510. Similarly, the anvil 68 can be modified to include a single row of staple forming grooves 512, or three or more rows of staple forming grooves 512.

Figure 28:
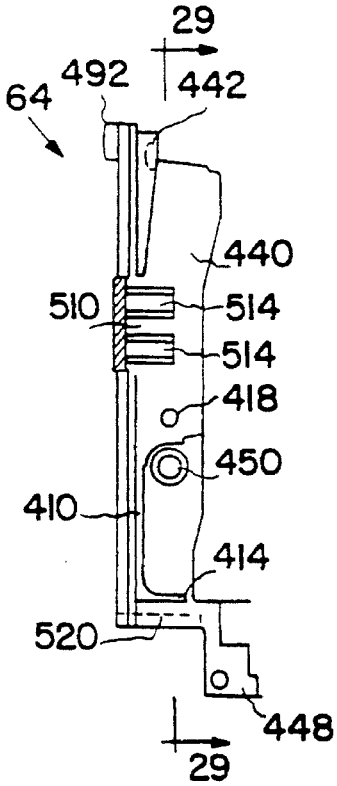
FIG. 28 is an enlarged, partially cutaway side view of the staple cartridge of the stapling head assembly.
Figure 29:
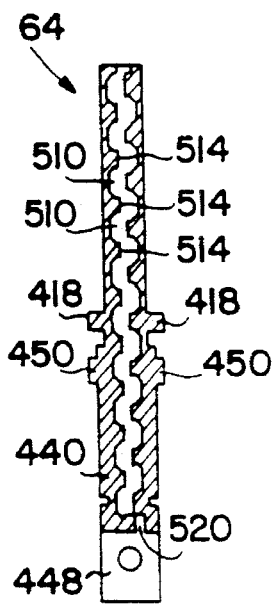
FIG. 29 is an enlarged vertical section of the staple cartridge along line 29—29 of FIG. 28.

As shown in FIG. 29, the staple receiving pockets 510 in each row are separated by a series of horizontal ribs 514 which serve as guides for the staples 65. The staple cartridge housing 440 includes a pair of elongated flanges 516 (FIG. 27) extending along its opposite sides which serve as cutting guides for a surgical knife or scalpel. An elongated notch 520 (FIGS. 28 and 29) extends horizontally across the bottom of the staple cartridge housing 440 for receiving a corresponding ridge 522 (FIG. 26) formed on the base member 370 of the anvil 68. The channel 520 and the ridge 522 act as a guide mechanism for aligning the anvil 68 with the staple cartridge 64 when the movable jaw 66 is pulled toward the fixed jaw 62.

Figure 30:
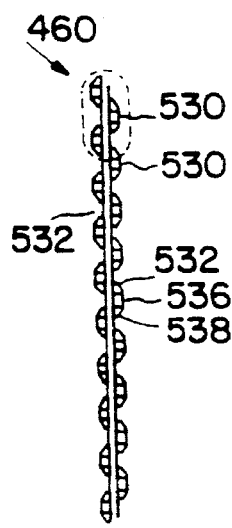
FIG. 30 is an enlarged front or distal view of the staple driver of the stapling head assembly.
Figure 31:
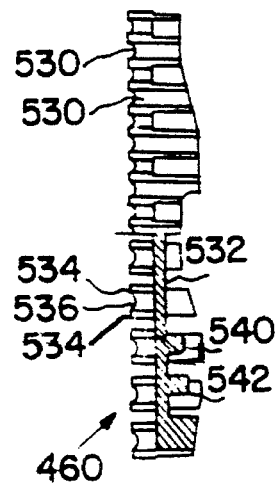
FIG. 31 is a partially cutaway side view of the staple driver of FIG. 30.

Referring to FIGS. 30 and 31, the staple driver 460 includes a plurality of staple driving fingers 530 mounted on a central connecting web 532 and arranged in two staggered rows corresponding to the rows of staple receiving pockets 510 in the staple cartridge housing 440. The distal end of each staple driving finger 530 has a substantially hexagonal cross section and is slidably received in one of the staple forming pockets 510 which also has a substantially hexagonal shape. Each of the staple driving fingers 530 of the staple driver 460 is slidably received between an adjacent pair of ribs 514 (FIG. 29) within the staple cartridge housing 440. At its distal end, each of the staple driving fingers 530 has a pair of staple engaging ridges 534 separated by a transversely extending notch 536. A pair of staple receiving grooves 538 extends longitudinally across the ridges 534 on opposite sides of each notch 536.

Referring to FIGS. 16 and 31, the cam insert 462 is sandwiched between the two rows of staple driving fingers 530 on the proximal side of the connecting web 532 to strengthen the staple driver 460. A pair of positioning fingers 540 and 542 project proximally from the central connecting web 532 in the space between the staple driving fingers 530 on the staple driver 460. The positioning fingers 540 and 542 are received in a pair of notches 544 and 546 formed at the distal edge of the staple driver insert 462 to facilitate the assembly of the staple driver 460 and the staple driver insert 462 in the proper orientation.

Referring to FIG. 9, the stapling head assembly 60 includes a detent or lock pin 550 for retaining the firing cam 464 in an unfired position before the firing of the staple 65 in the stapling head assembly 60. The lock pin 550 has a hollow resilient finger 552 which is snap-fit into a hole formed at the rear of the cover 424. The firing cam 464 includes a proximally projecting ledge 554 which is disposed above the resilient finger 552 before the staples 65 are fired to retain the firing cam 464 in its unfired position. When the firing cam 464 is pulled downward by the firing cable 190, the ledge 554 flexes the resilient finger 552 out of its way to permit the firing cam 464 to move downward to actuate the staple driver 460 and fire the Staples 65.

Preferably, the firing cable 190 is a braided cable made of stainless steel filaments. The closure cable 230 is made of a compliant material, e.g., Vectran™, manufactured by Hoechst-Celanese, which permits the closure cable to stretch when the stapling instrument 50 is operated. The strength of the cables 190 and 230 is designed to achieve the desired staple height at all orientations and articulation angles of the stapling head assembly 60. The compliant material of the closure cable 230 permits stretching when the stapling head assembly 60 is pivoted about the vertical axis 52 of the pivot connection 72 so that the force to close the jaws 62 and 66 remains substantially constant.

During the assembly of the stapling instrument 50, the length of the support shaft assembly 70 is adjusted by rotating the adjusting nut 140 to move the tubular support shaft 74 axially and to adjust the tension in the closure cable 230 for closing the jaws 62 and 66. By rotation of the adjusting nut 140, the overall length of the support shaft assembly 70 can be adjusted to set a sufficient tension in the closure cable 230 to completely close the jaws 62 and 66 when the jaw closure lever 84 is actuated. After the required tension is achieved, the half-sections 102 of the control knob 82 are assembled together with the adjusting nut 140. The longitudinal ribs 148 (FIG. 15) on the inside of the knob half-sections 102 are received in the grooves 146 on the adjusting nut 140 and in the grooves 152 of the flanges 150 to fix the shaft 74 and the adjusting nut 140 on the control knob 82 and to set the length of the support shaft assembly 70 and the tension in the closure cable 230.

It is desired that the closure cable 230 pull the anvil 68 toward the staple cartridge 64 with sufficient force to cause the head pin 342 to lock up in the guide slot 386 and to cause the slide pin 380 to lock up in the slots 382 and 384 so that the jaws 62 and 66 are completely closed by the jaw closure lever 84 to produce a uniform staple height when the staple firing lever 86 is actuated. When the head pin 342 and the slide pin 380 are locked up, the anvil 68 is locked in a closed position parallel to the staple cartridge 64 to provide a uniform spacing therebetween. The formed staple height is determined by the fixed distance between the anvil 68 and the staple cartridge 64 and is substantially independent of the tension in the closure cable 230 when the staple firing lever 86 is actuated.

Referring to FIGS. 18 and 20, as the anvil 68 is pulled toward its closed position by the closure cable 230, the tip of the anvil 68 initially contacts the tissue stop 492 on the staple cartridge 64. The upward movement of the anvil arm 368 is completed when the lower edge of the guide slot 386 bottoms out against the head pin 342 supported in the holes 340 (FIG. 14) of the head plate 328. The bearing pin 342 and the slide pin 380 are slightly smaller in diameter than the width of the anvil slots 382 and 386 to permit the anvil 68 to slide easily during the closure and opening of the jaws 62 and 66. The diameter of the bearing pin 342 is also slightly smaller than the diameter of the holes 340 in the head plate 328.

As shown in FIGS. 21 and 22, when the staple firing lever 86 is actuated, the firing cable 190 pulls the firing cam 464 downward to advance the staple driver 460 toward the anvil 68. The staple driver 460 drives the staples 65 from the staple cartridge 64 into contact with the anvil 68. The pressure of the staples 65 causes the tip of the anvil 68 to separate from the tissue stop 492 while the anvil 68 is pivoted in a counter-clockwise direction about the closure cable pin 394. The pivotal movement of the anvil 68 causes the slide pin 380 to be shifted proximally by the distal edge of the anvil slot 382 and to bear against the proximal edges of the slots 384 in the head plate 328. Similarly, the counter-clockwise pivoting of the anvil 68 causes the bearing pin 342 to be shifted proximally by the distal edge of the anvil slot 386 and to bear against the proximal sides of the holes 340 in the head plate 328.

The contact of the bearing pin 342 with the anvil slot 386 and the holes 340 and the contact of the slide pin 380 with the anvil slot 382 and the slots 384 provide a binding action between the anvil 68 and the head plate 328. This binding action locks the anvil arm 368 in a predetermined vertical position which is attained when the lower edge of the anvil slot 386 contacts the bottom of the bearing pin 342 in response to the tension of the closure cable 230. Also, the binding action results in a formed staple height substantially independent of the tension or strength of the closure cable 230. As a result, the formed height of the staples 65 is more easily controllable and consistent.

When the staples 65 are forced against the anvil 68 by the staple driver 460, the staples 65 are formed into a desired B-shaped configuration (FIG. 22). Although the anvil 68 deflects under the load of the staple forming forces, the anvil arm 368 does not move vertically downward due to the binding action described above. After the staples 65 are completely formed into the B-shaped configuration, the force of the staples 65 pressing on the anvil 68 is diminished thereby allowing the anvil 68 to return to an unloaded state and to pivot in a clockwise direction. The pivoting of the anvil 68 toward its original position causes the bearing pin 342 and the slide pin 380 to shift back to the positions where the binding action between the anvil 68 and the head plate 328 is released. The anvil 68 is released from its locked position and is easily pushed to its open position by the compression return spring 396 when the tension in the closure cable 230 is released by actuation of the release button 100.

The invention in its broader aspects is not limited to the specific details of the preferred embodiments shown and described, and those skilled in the art will recognize that the invention can be practiced with modification within the spirit and scope of the appended claims.

We claim:

1. A surgical stapling instrument for applying one or more surgical staples to tissue, comprising:
    a stapling head assembly including a first jaw with a staple holder for receiving one or more surgical staples a second jaw with an anvil for clamping the tissue against said staple holder when said jaws are closed, and a staple driver for driving the staples from said staple holder into the tissue and against said anvil;
    an actuator handle assembly including a jaw closure lever for closing said jaws and a staple firing lever for actuating said staple driver;
    a closure cable operable by said jaw closure lever for closing said jaws to clamp the tissue between said anvil and said staple holder;
    a firing cable operable by said staple firing lever for actuating said staple driver to drive the staples into the tissue and against said anvil; and
    a pulley rotatably mounted on said actuator handle assembly about a fixed axis and secured to said an end of firing cable for applying tension to said firing cable when said pulley is rotated by said staple firing lever to actuate said staple driver.

2. The surgical instrument of claim 1, which includes:
    drive means coupling said staple firing lever to said pulley for rotating said pulley when said staple firing lever is actuated to apply tension to said firing cable to actuate said staple driver.

3. The surgical instrument of claim 2, wherein said drive means comprises:
    a pair of drive gears rotatably positioned on opposite sides of said pulley, said drive gears having a set of drive lugs positioned for movement into engagement with a set of side lugs on said pulley when said drive gears are rotated; and
    a pair of gear sectors on said staple firing lever engaged with said drive gears for rotating said drive gears when said staple firing lever is actuated to move said drive lugs into engagement with said side lugs to rotate said pulley and to apply tension to said firing cable.

4. The surgical instrument of claim 1 wherein:
    said pulley includes a contoured cam lobe for actuating said firing cable with different mechanical advantages as said pulley is rotated.

5. The surgical instrument of claim 4, wherein:
    said cam lobe includes a first cam region with a large lobe height to provide a small mechanical advantage for actuating said firing cable, a second cam region with an intermediate lobe height which provides an increased mechanical advantage, and a third cam region with a small lobe height which provides a large mechanical advantage.

6. The surgical instrument of claim 1, which includes:
    anti-backup means for engaging said pulley to prevent the pay-out of said firing cable before and after said staple firing lever is actuated.

7. The surgical instrument of claim 1, which includes:
    latch means mounted on said actuator handle assembly for latching said jaw closure lever in a closed position when said jaws are closed; and
    a manually operable release button mounted on said actuator handle assembly for actuating said latch means to unlatch said jaw closure lever and allow said jaw closure lever to return to an open position to open said jaws.

8. The surgical instrument of claim 1, which includes:
    an anti-backup member on said actuator handle assembly located adjacent to the periphery of said pulley;
    a first detent on said pulley for engaging said anti-backup member to stop the rotation of said pulley in a first position and prevent the pay-out of said firing cable before said staple firing lever is actuated; and
    a second detent on said pulley for engaging said anti-backup member to stop the rotation of said pulley in a second position and prevent the pay-out of said firing cable after said staple firing lever is actuated.

9. A surgical stapling instrument for applying one or more surgical staples to tissue, comprising:
    a stapling head assembly including a proximal jaw which supports a staple holder for receiving one or more surgical staples, a distal jaw which supports an anvil for clamping the tissue against said staple holder when said jaws are closed, and a staple driver for driving the staples into the tissue and against said anvil;
    an actuator handle assembly including a jaw closure lever for closing said jaws and a staple firing lever for actuating said staple driver;
    a closure cable operable by said jaw closure lever for moving said distal jaw relative to said proximal jaw to clamp the tissue between said anvil and said staple holder;
    a firing cable operable by said staple firing lever for actuating said staple driver to drive the staples into the tissue and against said anvil; and
    a pulley rotatably mounted on said actuator handle assembly about a fixed axis and secured to an end of said firing cable for applying tension to said firing cable when said pulley is rotated by said staple firing lever to actuate said staple driver.

10. The surgical instrument of claim 9, which includes:

drive means coupling said staple firing lever to said pulley for rotating said pulley when said staple firing lever is actuated to apply tension to said firing cable to actuate said staple driver.

11. The surgical instrument of claim 10, wherein said drive means comprises:

a pair of drive gears rotatably positioned on opposite sides of said pulley, said drive gears having a set of drive lugs positioned for movement into engagement with a set of side lugs on said pulley when said drive gears are rotated; and a pair of gear sectors on said staple firing lever engaged with said drive gears for rotating said drive gears when said staple firing lever is actuated to move said drive lugs into engagement with said side lugs to rotate said pulley and to apply tension to said firing cable.

12. The surgical instrument of claim 9, wherein:

said pulley includes a contoured cam lobe for actuating said firing cable with different mechanical advantages as said pulley is rotated.

13. The surgical instrument of claim 12, wherein:

said cam lobe includes a first cam region with a large lobe height to provide a small mechanical advantage for actuating said firing cable, a second cam region with an intermediate lobe height which provides an increased mechanical advantage, and a third cam region with a small lobe height which provides a large mechanical advantage.

14. The surgical instrument of claim 9, which includes:

anti-backup means for engaging said pulley to prevent the pay-out of said firing cable before and after said staple firing lever is actuated.

15. The surgical instrument of claim 9, which includes:

an anti-backup member on said actuator handle assembly located adjacent to the periphery of said pulley;

a first detent on said pulley for engaging said anti-backup member to stop the rotation of said pulley in a first position and prevent the pay-out of said firing cable before said staple firing lever is actuated; and a second detent on said pulley for engaging said anti-backup member to stop the rotation of said pulley in a second position and prevent the pay-out of said firing cable after said staple firing lever is actuated.

16. The surgical instrument of claim 9, which includes:

latch means mounted on said actuator handle assembly for latching said jaw closure lever in a closed position when said jaws are closed; and a manually operable release button mounted on said actuator handle assembly for actuating said latch means to unlatch said jaw closure lever and allow said jaw closure lever to return to an open position to open said jaws.

* * * * *